US011908568B2

United States Patent
Xia et al.

(10) Patent No.: US 11,908,568 B2
(45) Date of Patent: Feb. 20, 2024

(54) SYSTEM AND METHODS FOR RADIOGRAPHIC IMAGE QUALITY ASSESSMENT AND PROTOCOL OPTIMIZATION

(71) Applicants: CANON MEDICAL SYSTEMS CORPORATION, Otawara (JP); University Health Network, Toronto (CA)

(72) Inventors: Ting Xia, Vernon Hills, IL (US); Zhou Yu, Vernon Hills, IL (US); Patrik Rogalla, Toronto (CA); Bernice Hoppel, Vernon Hills, IL (US)

(73) Assignees: CANON MEDICAL SYSTEMS CORPORATION, Otawara (JP); University Health Network, Toronto (CA)

( * ) Notice: Subject to any disclaimer, the term of this patent is extended or adjusted under 35 U.S.C. 154(b) by 600 days.

(21) Appl. No.: 17/077,413

(22) Filed: Oct. 22, 2020

(65) Prior Publication Data
US 2022/0130520 A1 Apr. 28, 2022

(51) Int. Cl.
G06T 7/00 (2017.01)
G16H 30/20 (2018.01)
(Continued)

(52) U.S. Cl.
CPC .............. *G16H 30/20* (2018.01); *G06N 3/04* (2013.01); *G06T 7/0014* (2013.01); *G16H 50/20* (2018.01);
(Continued)

(58) Field of Classification Search
CPC ........ G16H 30/20; G16H 50/30; G16H 50/20; G06V 3/04; G06T 7/0014
See application file for complete search history.

(56) References Cited

U.S. PATENT DOCUMENTS 8,412,544 B2 4/2013 Reiner
9,918,700 B2 3/2018 El-Zehiry et al.
(Continued)

OTHER PUBLICATIONS

Joscha Maier et al., "Real-Time Patient-Specific CT Dose Estimation for Single- and Dual-Source CT using a Deep Convolutional Neural Network," Feb. 27, 2019, Deutsches Krebsforschungszentrum in Der Helmholtz/Gemeinschaft (18 pages).
(Continued)

*Primary Examiner* — Edward Park
(74) *Attorney, Agent, or Firm* — Oblon, McClelland, Maier & Neustadt, L.L.P.

(57) ABSTRACT

The present disclosure relates to a method for patient-specific optimization of imaging protocols. According to an embodiment, the present disclosure relates to a method for generating a patient-specific imaging protocol, comprising acquiring scout scan data, the scout scan data including scout scan information and scout scan parameters, generating a simulated image based on the acquired scout scan data, deriving a simulated dose map from the generated simulated image, determining image quality of the generated simulated image by applying machine learning to the generated simulated image, the neural network being trained to generate at least one probabilistic quality representation corresponding to at least one region of the generated simulated image, evaluating the determined image quality relative to a image quality threshold and the derived simulated dose map relative to a dosage threshold, optimizing. based on the evaluating, scan acquisition parameters and image reconstruction parameters, and generating, optimal imaging protocol parameters, wherein the optimal imaging protocol parameters maximize image quality while minimizing radiation exposure.

20 Claims, 24 Drawing Sheets

(51) Int. Cl.
G06N 3/04 (2023.01)
G16H 50/30 (2018.01)
G16H 50/20 (2018.01)

(52) U.S. Cl.
CPC ... *G16H 50/30* (2018.01); *G06T 2207/10028* (2013.01); *G06T 2207/10081* (2013.01); *G06T 2207/30168* (2013.01)

(56) References Cited

U.S. PATENT DOCUMENTS

| | | | | |
|---|---|---|---|---|
| 2015/0265224 | A1* | 9/2015 | Gerland | G16H 50/30 382/131 |
| 2016/0279444 | A1* | 9/2016 | Schlosser | A61N 5/1049 |
| 2018/0144214 | A1 | 5/2018 | Hsieh et al. | |
| 2018/0330818 | A1 | 11/2018 | Hseih et al. | |

OTHER PUBLICATIONS

Sigal Trattner et al., "Standardization and Optimization of Computed Tomography Protocols to Achieve Low-Dose," Journal of the American College of Radiology. Mar. 2014; 11(3): 271-278.; (14 pages).

James Kofler et al., "CT Protocol Review and Optimization," Journal of the American College of Radiology. Mar. 3, 2014, 11(3): 267-270y (4 pages).

F.R. Verdun, et al., "Image quality in CT: From physical measurements to model observers," http://www.physicamedica.com; Oct. 12, 2015 (21 pages).

Justin Solomon et. al., "Quantitative comparison of noise texture across CT scanners from different manufactures," Medical Physics, vol. 39 (10). Oct. 2012 (8 pages).

Baiyu Chen et. al., "Assessment of volumetric noise and resolution performance for linear and nonlinear CT reconstruction methods," Medical Physics, vol. 41, No. 7, Jul. 2014, (13 pages).

Hao Gong, et al., HHS Public Access; "Correlation between model observers in uniform background and human observers in patient liver background for a low-contrast detection task in CT"; Proc SPIE Int Soc Opt Eng. Feb. 2018; (12 pages).

Hao Gong, et al; "A deep learning—and partial least square regression-based model observer for a low-contrast lesion detection task in CT"; Med. Phys. 46 (5), May 2019 (12 pages).

Zhye Yin, et. al., "Image Quality Metric Extraction Based on Machine Learning Techniques for Clinical CT Protocol Optimization," RSNA Annual Meeting, 2018, Chicago, USA (2 pages).

Juan Montoya, et. al, "Three-Dimensional CT Scout from Conventional Two-View Radiograph Localizers Using Deep Learning," RSNA Annual Meeting, 2018, Chicago, USA (2 pages).

\* cited by examiner

FIG. 2B

| SCAN ACQUISITION PARAMETERS | | |
|---|---|---|
| COLLIMATION THICKNESS | USE OF PHOTON-COUNTING | |
| CALIBRATED FIELD OF VIEW | SAMPLING FREQUENCY | |
| DYNAMIC BOWTIE FILTER | EXPOSURE | |
| PITCH | | |
| ROTATION SPEED | | |
| X-RAY BEAM ENERGY | | |
| TUBE CURRENT | | |

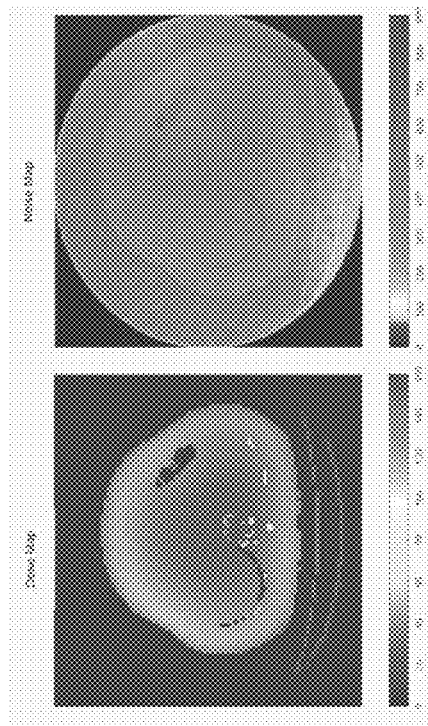
FIG. 2H
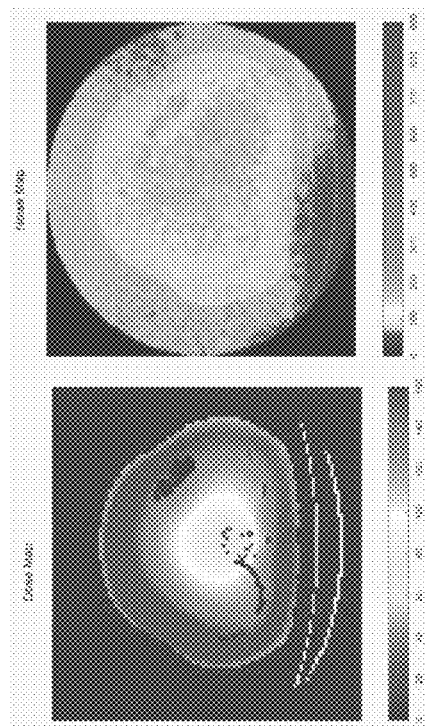
FIG. 2I
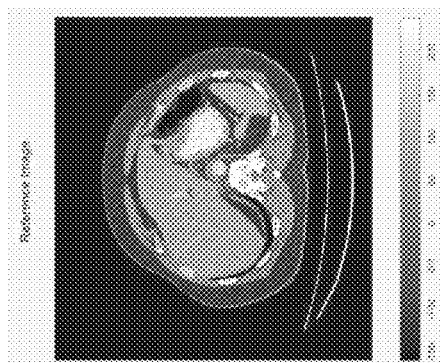
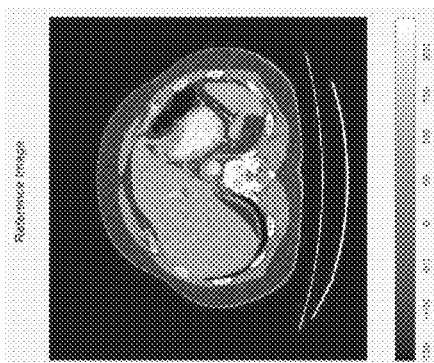

SYSTEM AND METHODS FOR RADIOGRAPHIC IMAGE QUALITY ASSESSMENT AND PROTOCOL OPTIMIZATION

BACKGROUND

Field of the Disclosure

The present disclosure relates to a system and method for optimization of imaging protocols based on patient and application demands.

Description of the Related Art

As it relates to computed tomography (CT) imaging, it is appreciated that imaging protocols impact image quality and radiation dose of a majority of CT scans. Imaging protocols comprise myriad variables including scan acquisition parameters such as gantry rotation time, tube current, tube voltage, pitch, field of view, and contrast agent timing, as well as image reconstruction parameters such as reconstruction kernels, reconstruction algorithms, matrix size (e.g., 512, 1024), slice thickness, and patient-size dependent parameters. Given the breadth of parameters that can possibly be modified, general practice dictates that certain universally-applicable values of each parameter be implemented in order to make the task practicable.

Such approach, however, is understandably not ideal for every patient. In fact, it may be important that each patient receives a unique imaging protocol in order to maximize image quality while minimizing radiation exposure. An efficient tool for predicting clinical images for protocol optimization and evaluating these factors, however, is not available. To this end, an effective image quality assessment tool for clinical images, one that does not require direct input of a clinician, is missing from present imaging protocols. As a result, though desirable to provide patient-specific and task-specific protocol optimization, which may be useful for longitudinal studies, long-term radiation dose monitoring, and individualized medicine, such customization is not presently available.

Accordingly, the present disclosure describes a system and apparatus for developing patient- and task-specific imaging protocols.

The foregoing "Background" description is for the purpose of generally presenting the context of the disclosure. Work of the inventors, to the extent it is described in this background section, as well as aspects of the description which may not otherwise qualify as prior art at the time of filing, are neither expressly or impliedly admitted as prior art against the present invention.

SUMMARY

The present disclosure relates to a system, apparatus, method, and non-transitory computer-readable storage medium for patient-specific imaging protocol optimization.

According to an embodiment, the present disclosure relates to a method for generating a patient-specific imaging protocol using a neural network having been trained to generate at least one probabilistic quality representation corresponding to at least one region of a generated simulated image, comprising receiving, by processing circuitry, scout scan data, the received scout scan data including scout scan information and scout scan parameters, generating, by the processing circuitry, the generated simulated image based on the received scout scan data, scan acquisition parameters, and image reconstruction parameters, deriving, by the processing circuitry, a simulated dose map from the received scout scan data and the scan acquisition parameters, evaluating, by the processing circuitry, a determined image quality of the generated simulated image relative to a predetermined image quality threshold and the derived simulated dose map relative to a predetermined dosage threshold, and generating, by the processing circuitry and based on the evaluating, imaging protocol parameters based on the scan acquisition parameters and the image reconstruction parameters. The method further comprises generating, by the processing circuitry and based on the evaluating, a subsequent generated simulated image based on the received scout scan data, subsequent scan acquisition parameters, and subsequent image reconstruction parameters, deriving, by the processing circuitry, a subsequent simulated dose map from the received scout scan data and the subsequent scan acquisition parameters, evaluating, by the processing circuitry, a determined image quality of the subsequent generated simulated image relative to the predetermined image quality threshold and the subsequent derived simulated dose map relative to the predetermined dosage threshold, and generating, by the processing circuitry and based on the evaluating, subsequent imaging protocol parameters based on the subsequent scan acquisition parameters and the subsequent image reconstruction parameters, the subsequent imaging protocol parameters increasing image quality while reducing radiation exposure.

The foregoing paragraphs have been provided by way of general introduction, and are not intended to limit the scope of the following claims. The described embodiments, together with further advantages, will be best understood by reference to the following detailed description taken in conjunction with the accompanying drawings.

BRIEF DESCRIPTION OF THE DRAWINGS

A complete appreciation of the disclosure and many of the attendant advantages thereof will be readily obtained as the same becomes better understood by reference to the following detailed description when considered in connection with the accompanying drawings, wherein:

FIG. 2B is a schematic of scan acquisition parameters, according to an exemplary embodiment of the present disclosure;

FIG. 2H is an illustration of a dose map and a noise map of a CT image at a first set of acquisition parameters, according to an exemplary embodiment of the present disclosure;

FIG. 2I is an illustration of a dose map and a noise map of a CT image at a second set of acquisition parameters, according to an exemplary embodiment of the present disclosure;

DETAILED DESCRIPTION

Figure 1:
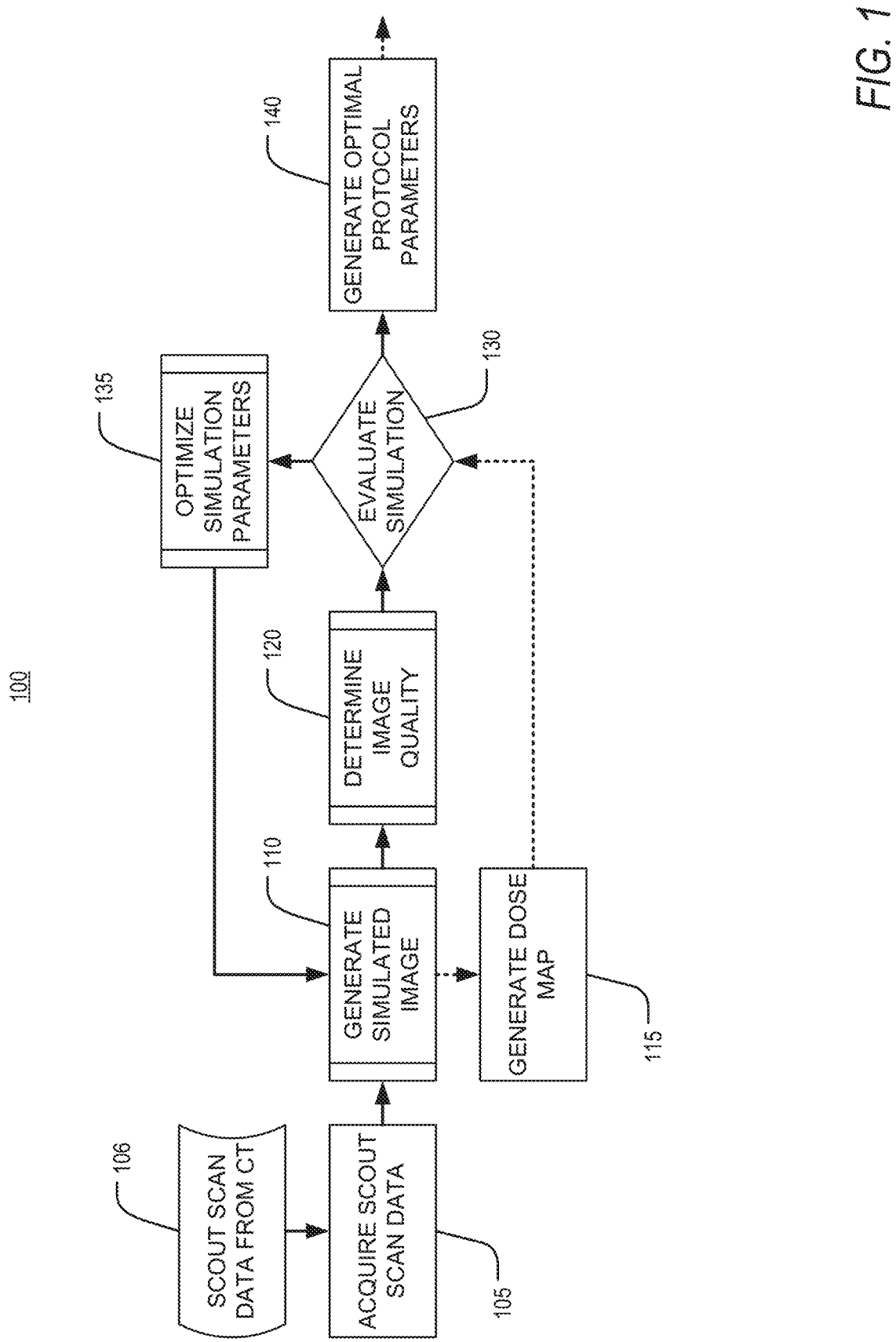
FIG. 1 is a flow diagram of a method of generating a patient-specific imaging protocol, according to an exemplary embodiment of the present disclosure.

The terms "a" or "an", as used herein, are defined as one or more than one. The term "plurality", as used herein, is defined as two or more than two. The term "another", as used herein, is defined as at least a second or more. The terms "including" and/or "having", as used herein, are defined as comprising (i.e., open language). Reference throughout this document to "one embodiment". "certain embodiments", "an embodiment", "an implementation". "an example" or similar terms means that a particular feature, structure, or characteristic described in connection with the embodiment is included in at least one embodiment of the present disclosure. Thus, the appearances of such phrases or in various places throughout this specification are not necessarily all referring to the same embodiment. Furthermore, the particular features, structures, or characteristics may be combined in any suitable manner in one or more embodiments without limitation.

One of the long-recognized perils of medical imaging is the use of ionizing radiation. For instance, it is known that risk of carcinogenesis increases with increasing exposure to ionizing radiation. A number of diagnostic medical imaging modalities and applications utilize ionizing radiation, including radiography, mammography, computed tomography (CT), nuclear medicine, and other forms of molecular imaging. In addition to diagnostic applications, ionizing radiation may be used in therapeutic radiology for treatment of patients with various forms of cancer. Collectively, these diagnostic and therapeutic medical applications pose understood iatrogenic risk to the patient and must be justified through risk-benefit analyses to substantiate the medical efficacy of use.

Thus, while radiation safety and medical imaging quality may be viewed in isolation, reality dictates that they are often directly related to one another. A given medical imaging procedure (e.g., abdominal CT examination) can be associated with a quantifiable amount of ionizing radiation, which is dependent upon the scan acquisition parameters selected, the technology utilized, and various attributes of the patient for which the examination is being performed. If one were to attempt to adjust the scan acquisition parameters in an attempt to reduce radiation dose, overall image quality would be concurrently impacted, largely due to increased pixel noise and/or quantum noise As a result, attempts to modify radiation dose (i.e., to improve radiation safety) without determining the resultant impact on image quality are misguided. Radiation dose and image quality are inextricably related to one another and, as a result, should be considered in combination.

Such considerations of the balance between radiation and image quality, however, are muddled when needs of specific patients are considered. This balance may be complicated by regional variations within different patients and by variations within each imaging volume which might otherwise be addressed by consideration of task-specific needs. For instance, an abdominal CT examination may feature a variety of tissues serving a variety of functions, however, as it relates to imaging, these varied tissues attenuate and scatter photons differently and must be considered differently, even within a same imaging volume. It can be appreciated that, in addition to already known differences between patients, imaging protocol optimization is not a trivial problem.

It is, therefore, understandable that most current imaging protocols available are generalized to a broad population and, therefore, do not provide customized, patient-specific, and application-dependent functionality. Understanding that physicians routinely check medical image quality for various quality-related factors, such as artifacts, spatial resolution, contrast, and noise, it becomes difficult to envisage a method whereby an imaging protocol may be so focused as to be tuned for individual patients, diseases, and organs of interest while requiring clinician intervention at each step of optimization.

To this end, and according to an embodiment, the present disclosure describes a method for imaging protocol optimization that is body part-, task-, disease-, and otherwise patient-specific while maximizing image quality for diagnosis and minimizing radiation exposure to a patient. The approach is a machine learning-based approach that utilizes neural networks trained according to clinician evaluations of medical images. Such approach provides consistency within and among different scanner types and improves throughput and technology efficiency.

In an embodiment, the present disclosure describes an artificial intelligence-based system for automated image quality assessment and protocol optimization. The system may include a computer simulation tool that can simulate CT images, which may be simulated two-dimensional (2D) CT images and/or simulated three-dimensional (3D) CT images, and corresponding dose map(s), from acquired scout scan information and scout scan conditions.

The system may include an image quality assessment tool, such as a blind image quality assessment tool, to predict and score medical image quality of each of the simulated CT images, without full reference. The predictions and scores may be made for, in an example, at least one region within a slice of a simulated 2D CT image, a single slice of a simulated 2D CT image or simulated 3D CT image, at least one region within multiple slices of a simulated 3D CT image, and/or multiple slices of a simulated 3D CT image. For either a simulated 2D CT image or a simulated 3D CT image, the at least one region may be a single pixel or more than one pixel within a pixel area. The system may include a protocol optimization tool that can optimize protocol parameters (e.g., scan acquisition parameters, image reconstruction parameters) based on the image quality assessment and the dose map(s) to maximize image quality for diagnosis while minimizing radiation exposure to the patient. For instance, the protocol optimization tool may determine, based on differences in image quality assessment scores, protocol parameters for each of the at least one region within the slice of the simulated 2D CT image such that different protocol parameters may be implemented within different ones of the at least one region within the slice of the simulated 2D CT image.

Moreover, the above-described system may be implemented within a closed-loop solution for protocol simulation. The optimized protocol, based on the acquired scout scan information and scout scan conditions, can be implemented within a full CT scan of the patient.

Turning now to the Figures, FIG. 1 is a flow diagram of an artificial intelligence-based system for automated image quality assessment and protocol optimization, as introduced above. The flow diagram of FIG. 1 describes method 100.

Generally, prior to submitting a patient to a full CT scan (i.e., full radiation dose), and in order to confirm positioning of the patient relative to the imaging area, a scout scan may be performed. The scout scan may be a 2D scout scan including data from a single transaxial slice or may be a 3D scout scan including data from multiple transaxial slices. The scout scan may expose the patient to radiation on the level of a single chest radiograph, which may be a fraction of a radiation dose of a full CT scan. In the present disclosure, scout scan data may be used to iteratively simulate and evaluate a reconstructed image to determine theoretical scan acquisition parameters and theoretical image reconstruction parameters that are optimal for diagnostic purposes when implemented within a full CT scan. The optimized theoretical scan parameters and theoretical image reconstruction parameters may be based on a variety of patient-specific factors, including patient size, as may be determined from the acquired scout scan, disease type, and region of interest in view of image quality assessment of the simulated image, as informed by a clinician, and radiation exposure. Moreover, the optimized theoretical scan parameters and theoretical image reconstruction parameters may, for example, be the same for each pixel area of the simulated image and/or may be uniquely determined for each pixel area of the simulated image. For instance, the optimized theoretical scan parameters and theoretical image reconstruction parameters may be the same for each pixel area of a given transaxial slice of a simulated image or may be different for each pixel area thereof, the different parameter values instead populating a parameter map such that different parameter values describe each pixel area within the parameter map. Use of the acquired scout scan data for this approach ensures optimal imaging parameters. Determination of the quality of the simulated image may be based on implementation of an artificial neural network. The artificial neural network may be selected as one of a variety of artificial neural networks trained on a subset of images or image datasets that may be representative of specific disease types, patient demographics, regions of interest, and the like. The optimized imaging protocol parameters may include, for instance, adapted rotation speeds for specific regions of a body of the patient. Such imaging protocol parameters will be described in greater detail in subsequent Figures. Having optimized the theoretical scan parameters and theoretical image reconstruction parameters, a full CT scan of the patient may be performed on the basis of the optimized protocol. In this way, a full CT scan of the patient may be acquired in a way that ensures sufficient diagnostic information is obtained while minimizing radiation exposure to the patient.

Returning to FIG. 1, at step 105 of method 100, scout scan data of a patient can be acquired from a CT scanner at step 106 of method 100. The scout scan data may be data acquired by a 2D scout scan or a 3D scout scan, as introduced above. In an example, the scout scan data may be used to confirm only a region of interest of the patient. To this end, in one instance, the scout scan may be collected at a level of radiation equivalent to ~10 chest radiographs. The scout scan data can be used, subsequently, at sub process 110 of method 100 to simulate images.

At sub process 110 of method 100, the scout scan data acquired at step 105 of method 100 can be used to generate a simulated image. The simulated image may be a simulated 2D image or a simulated 3D image based on an acquired 2D scout scan or an acquired 3D scout scan. Further, the simulated image can be based on an initial set of scan acquisition parameters and image reconstruction parameters. In an embodiment, the simulated image may be based on previous scan data including previous sets of scan acquisition parameters and image reconstruction parameters. For clarity, the generated simulated image is a simulated 2D CT image based on data from an acquired 3D scout scan and description of method 100 is directed to implementation of method 100 in view of at least one region of the simulated 2D CT image, wherein the at least one region is a pixel area including 25 square pixels. Though the at least one region described above includes a 25 square pixel pixel area, it can be appreciated that the at least one region may be any fraction of a full area of a simulated 2D CT image and may be, in an example, the full area of the simulated 2D CT image such that there is only one at least one region.

Concurrently, at step 115 of method 100, radiation exposure may be estimated and a dose map(s) may be generated based on the generated simulated image (e.g., based on the acquired scout scan data and the scan acquisition parameters). To this end, the dose map may be a 2D dose map or a 3D dose map. In an embodiment, the dose map may reflect regional differences in parameters of an imaging protocol. As described above, the generated dose map will be used alongside the determined image quality to evaluate the image simulation and determine optimal imaging protocol parameters.

At sub process 120 of method 100, the quality of the image simulated at sub process 110 of method 100 can be determined. Generally, the quality of the image may be determined for at least one region within a slice of a simulated 2D CT image, for a single slice of a simulated 2D CT image or simulated 3D CT image, for at least one region within multiple slices of a simulated 3D CT image, and/or for multiple slices of a simulated 3D CT image. As introduced above, the quality of the image may be determined for at least one region of a simulated 2D CT image. Accordingly, the determined image quality may be represented by a matrix corresponding to the at least one region of the simulated 2D image. Image quality determination includes application of an artificial neural network for the generation of image quality assessment values and, subsequently, one or more score values that are representative of the image quality. Each score value may be, in an example, a scalar-transformed probabilistic quality representation.

The artificial neural network may be one selected from a group of artificial neural networks trained based upon hypothetical patient populations. For instance, though it can be appreciated that a generalized artificial neural network, representative of a diverse patient population, may be available, the artificial neural network may also be one trained to evaluate specific regions of interest, diseases of interest, and the like. In this way, the artificial neural network is tailored to value certain image attributes more or less than other image attributes based on the specific region of interest and/or disease being evaluated. Moreover, the above-described customized artificial neural networks can be trained to evaluate specific regions of interest, diseases of interest, and the like in view of diagnostic requirements relevant thereto. For instance, each customized artificial neural network may be trained according to training images assessed by clinicians, wherein different disease indications require different combinations of image quality attributes for diagnosis. As it relates to a combination of region specificity and disease specificity, it can be appreciated that a chest X-ray or a super low dose chest CT for a patient with lung disease may require different image quality attributes from a chest X-ray for a patient with a rib fracture. One may require low contrast detectability and the other may require higher spatial resolution. Moreover, different regions within a same chest X-ray may require different imaging protocols. By acknowledging the diagnostic variability of certain image quality attributes, each customized artificial neural network provides a tailored estimation of image quality assessment values as a probabilistic quality representation.

In an embodiment, each probabilistic quality representation may be transformed to one or more score values of the reconstructed image, each of one or more score values reflecting one or more imaging quality attributes of the simulated image. In an embodiment, the one or more score values may be generated for each region of a simulated 2D CT image, a plurality of one or more score values defining a regional map of score values, wherein each region of the simulated 2D CT image may be independently evaluated. The image quality determination of sub process 120 of method 100 will be described in greater detail with reference to subsequent Figures.

At step 130 of method 100, the image quality determined at sub process 120 of method 100 may be evaluated together with the dose map(s) generated at step 115 of method 100. In an embodiment, for each region of a simulated image, such evaluation may include a comparison of the determined image quality (e.g., one or more score values) to a predetermined threshold(s) of image quality (e.g., minimum score value(s)) as well as a comparison of the regional anticipated dosage to a threshold dosage (e.g., maximum radiation exposure). In this way, the determine image quality may be an evaluation of region variation of a simulated image.

In an embodiment, for each region, the one or more score values may be several values indicative of specific image quality attributes (e.g., contrast, artifacts, etc.). In an embodiment, for each region, the one or more score values may be a single value indicative of an average image quality within each region. The single value may be a probabilistic quality representation transformed into a scalar score.

In an embodiment, such evaluation may determine whether the scan acquisition parameters, image reconstruction parameters, and dosage are optimal. If the simulated image quality is deemed sufficient in view of radiation exposure considerations, the current scan acquisition parameters and image reconstruction parameters may define imaging protocol conditions for a full CT scan. However, if insufficient, an optimization may be performed, including sub process 135 of method 100, to identify the scan acquisition parameters and image reconstruction parameters that generate an image of sufficient diagnostic quality while providing a reduction in radiation exposure.

If it is determined, upon iterative evaluation at step 130 of method 100, that the scan acquisition parameters and image reconstruction parameters are optimal in view of regional image quality and radiation exposure, the iterative scan acquisition parameters and image reconstruction parameters can be generated as optimized imaging protocol parameters at step 140 of method 100 and implemented within a full CT scan of the patient.

Steps and sub processes introduced above will now be described in detail with reference to subsequent Figures. In particular, for clarity, the remainder of the description will assume image quality is determined for at least one region of a simulated 2D CT image generated in accordance with certain theoretical scan acquisition parameters and reconstruction parameters and based on a 3D CT image generated from acquired 3D scout scan data.

Figure 2A:
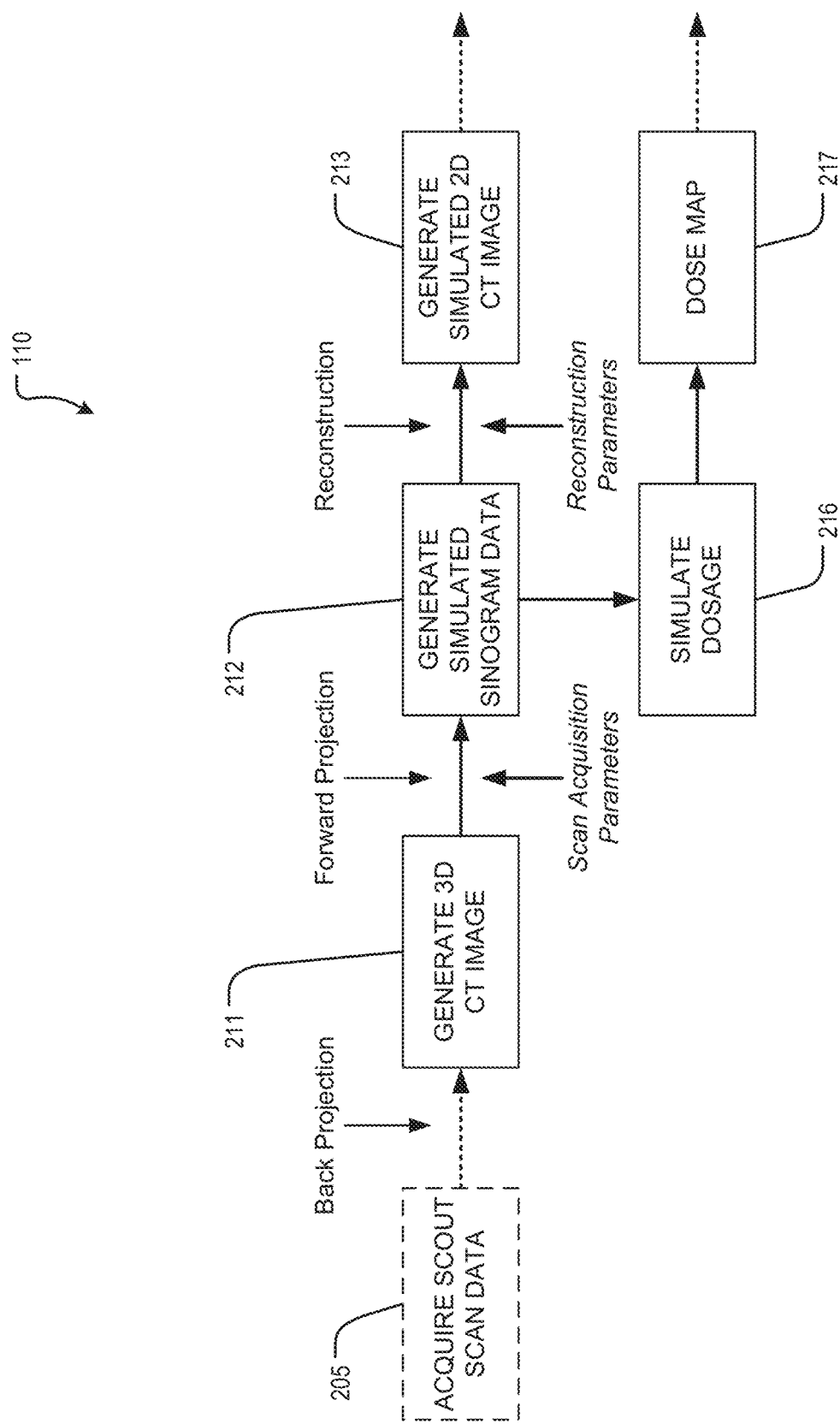
FIG. 2A is a flow diagram of a subprocess of a method of generating a patient-specific imaging protocol, according to an exemplary embodiment of the present disclosure.

FIG. 2A describes sub process 110 of method 100. At step 211 of sub process 110, scout scan data acquired at step 205 of method 100 can be used to generate, by back projection, a three-dimensional (3D) CT image. The 3D CT image generated at step 211 of sub process 110 may be used to generate simulated sinogram data at step 212 of method 110.

Regarding the simulated sinogram data generated at step 212 of sub process 110, the 3D CT image generated at step 211 of sub process 110 may be transformed by forward projection and according to scan acquisition parameters. Simulated dosage data may be generated at step 216 of method 110 based on the simulated sinogram data generated at step 212 of sub process 110. The dosage data simulated at step 216 of sub process 110 may be used to generate a dose map at step 217 of sub process 110, the generated dose map then being used at step 130 of method 100 during evaluation of simulated image quality in view of radiation exposure.

The scan acquisition parameters, as discussed above, may be theoretical scan acquisition parameters and may be modified, iteratively, during optimization to identify scan acquisition parameters that may be used for full CT imaging, understanding that each scan acquisition parameter impacts noise in the image and, thus, impacts radiation exposure. With reference to FIG. 2B, the scan acquisition parameters include, but are not limited to, pitch, rotation speed. X-ray beam energy (i.e., tube voltage), tube current, collimation thickness, calibrated field of view, a bowtie filter, sampling frequency, and whether photon-counting is used. Each of the scan acquisition parameters may be adjusted to a static variable or may be adjusted to a dynamic variable that is adjustable across a volume of a patient according to needs of the patient. For instance, soft tissues require lower tube current than harder tissues within the same imaging volume. Pitch can be defined as table movement per rotation divided by slice collimation. In helical CT, for instance, dose is inversely proportional to pitch. Rotation speed is the effective speed of gantry rotation. X-ray beam energy, or tube voltage, is the effective energy of the X-ray beam in units of kV. Tube current may be modulated in the x, y, and z direction of a scan and may be in units of mA. Collimation thickness is the thickness of detector elements within a CT system. The bowtie filter, which may be dynamic, is one of a variety of filters used to shape an X-ray beam and equalize its flux reaching different detector channels. Flux can be automatically changed during scanning with a self-adjusting bowtie filter. Sampling frequency may be adjusted in view of X-ray beam energy switching enabled by dual-energy CT. For instance, the sampling frequency may be changed based on the imaging task. A higher sampling frequency may be appropriate in fast-moving areas while a lower sampling frequency may be appropriate in 'slow-moving' areas, such as the abdomen. X-ray beam energy switching and tube current pulsing may be considered as dose reduction measures. Exposure may be adjusted dynamically based on the type of tissue imaged. The use of a photon-counting mode may be implemented based on the imaging task.

Figure 2C:
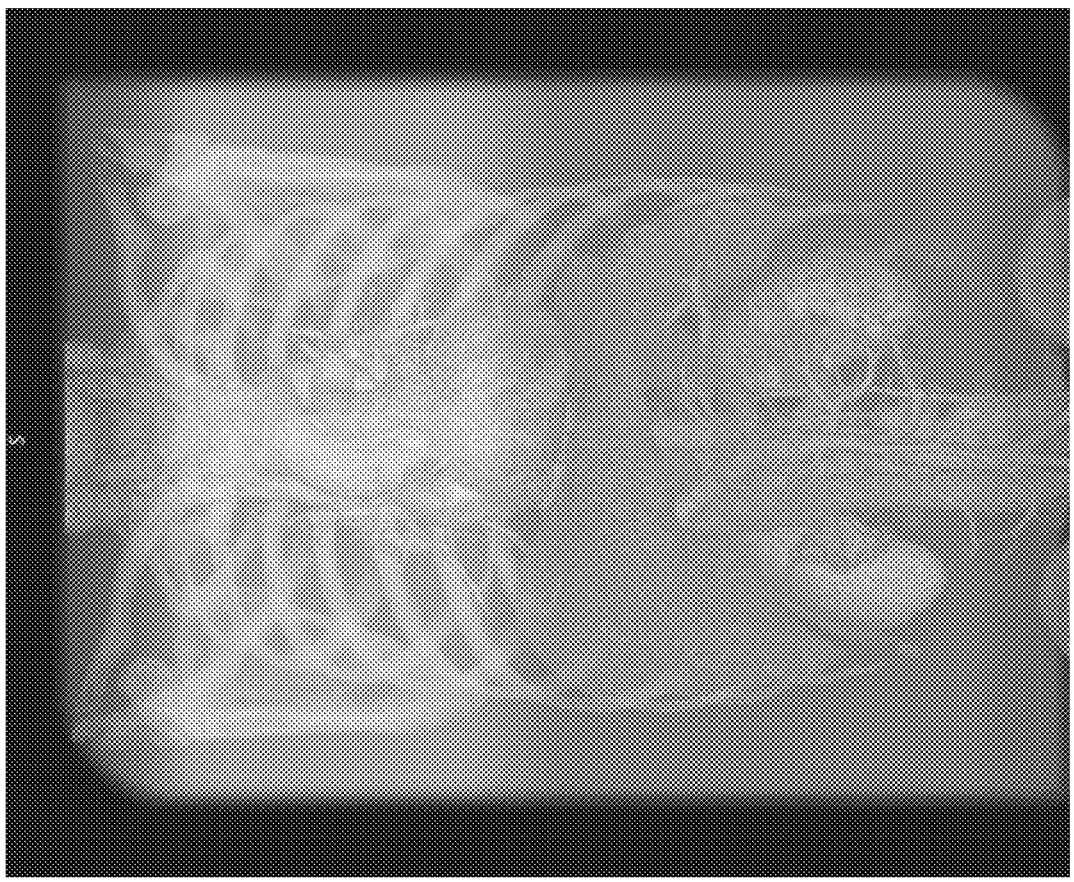
FIG. 2C is an illustration of a noise map of a computed tomography (CT) image, according to an exemplary embodiment of the present disclosure.

In an embodiment, tube current and X-ray beam energy may be modified according to a noise map of the patient generated from the acquired scout scan data. A 2D noise map, as shown in FIG. 2C, with regions of darker hue indicating regions of higher noise, illustrates noise in the patient. In an example, this allows a user to set a needed tube current, or mA, of the simulated scan to compensate for regions with high noise, such as the shoulders and the hips. In an embodiment, the tube current may be controlled within a single scan such that regions of high noise receive lower tube current while regions with low noise receive higher tube current. Additionally, the noise map can help set both the tube current and X-ray beam energy, or kV, to allow for the best contrast while ensuring penetration of the photons. In an embodiment, a noise map, as in FIG. 2C, may be used to combine detectors in regions where lower resolution is required such that noise may be lowered.

Figure 2D:
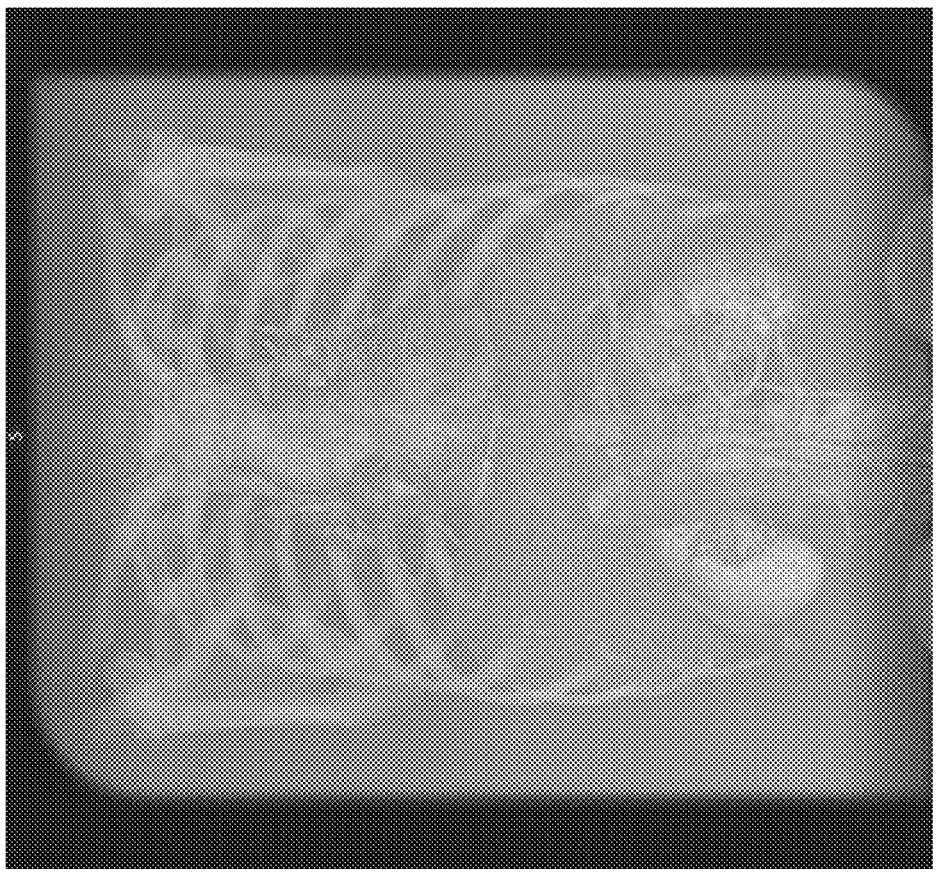
FIG. 2D is an illustration of a beam energy map, according to an exemplary embodiment of the present disclosure.

In an embodiment, X-ray beam energy may be modified according to densities of materials distributed throughout the patient. The effective energy of the X-ray beam determines the penetrance of the beam. Therefore, X-ray beam energy needs to be higher in regions with more dense material. For instance, as in FIG. 2D, a 2D X-ray beam energy map generated from the acquired scout scan data, it can be observed that the tissues of the abdomen and tissues of the upper torso have different densities and thus, require different kV values. Taken together with other scan acquisition parameters, such as tube current, and in view of the noise map of FIG. 2C, it can be appreciated that a balance is needed. A higher kV, for instance, may decrease low contrast detectability but is required to account for the density of bones in the shoulders and hips, which will block the penetration of X-rays. In another instance, the lungs and ribs can receive a higher kV with a lower mA, due to higher contrast objects. The abdomen, however, displays lower contrast and thus requires higher tube current with lower noise.

Figure 2E:
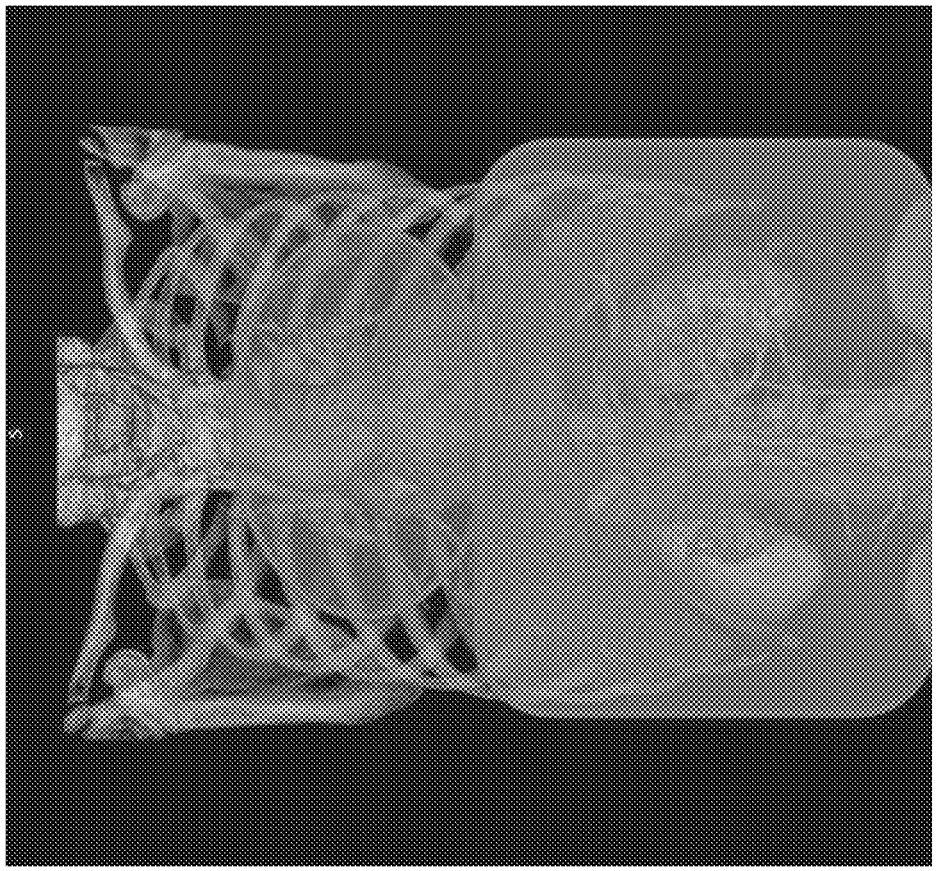
FIG. 2E is an illustration of a spatial resolution map, according to an exemplary embodiment of the present disclosure.

In an embodiment, gantry rotation speed may be modified in accordance with a 2D temporal resolution map generated from the acquired scout scan data. For instance, a decrease in rotation time of the gantry during CT imaging decreases motion artifacts and scan time but increases image noise and, in some cases, leads to streaking artifacts. Therefore, with reference to FIG. 2E, a CT scanner with the ability to modulate rotation time within a single scan may improve image quality by optimizing the speed of the gantry. For example, an understanding of a temporal resolution map allows for changes in rotation time in different regions of the body. As in FIG. 2E, the oval, upper region, corresponding to the cardiac region, may require much faster rotation than the rectangular, lower region, corresponding to the abdomen.

Figure 2F:
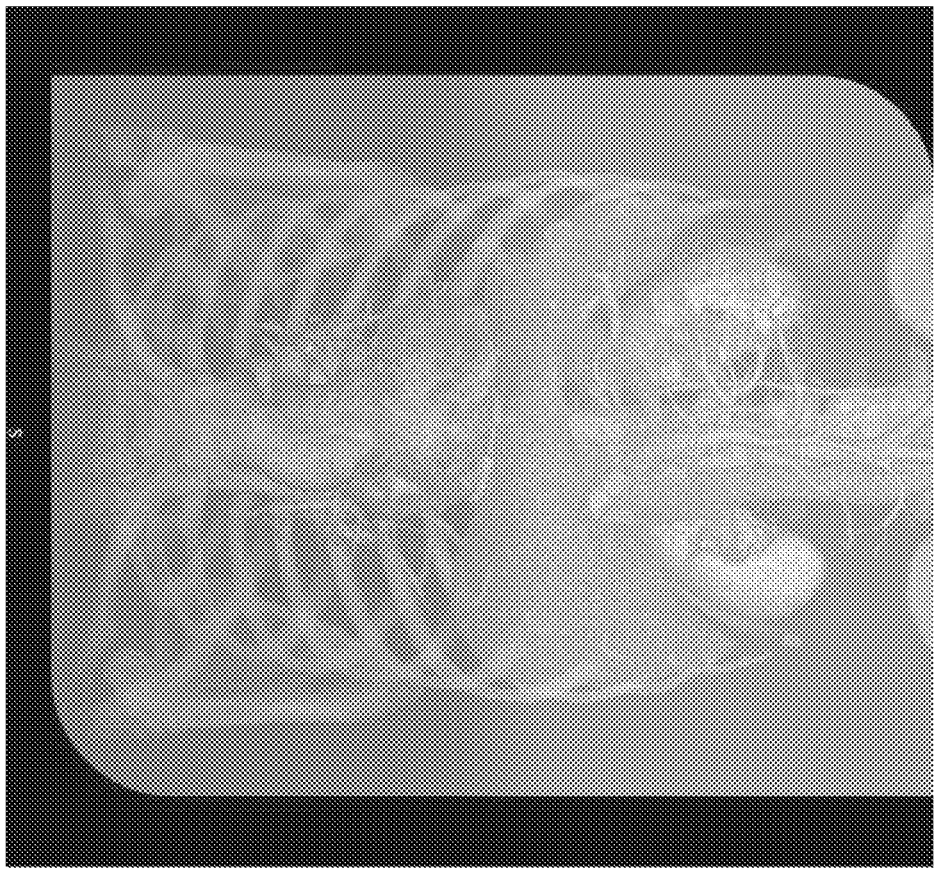
FIG. 2F is an illustration of a pitch and spatial resolution map, according to an exemplary embodiment of the present disclosure.

In an embodiment, pitch and matrix size (i.e. an image reconstruction parameter) may be modified in accordance with a 2D pitch map, or spatial resolution map, generated from acquired scout scan data. Pitch and matrix size can easily change with the CT scanner, as it is a function of table speed, rotation speed, and reconstruction matrix. Changing the pitch, therefore, effectively determines the sampling in the z-direction. Indicated by changing hues in the spatial resolution map of FIG. 2F, pitch may be higher in the chest region to gather high resolution data from small lung structures and vessels. In addition, the matrix size for reconstruction can also be increased in certain areas to improve resolution. Referring again to FIG. 2F, the abdomen may require less pitch and spatial resolution and so pitch and matrix can be lowered in this region to further lower the noise. In certain cases, detectors may also be combined in order to further lower the noise, though spatial resolution may be compromised. In an embodiment, and as it relates to method 100, described above, the reconstruction matrix can be optimized so that the voxel size (or pixel size in 2D) does not reduce the best possible spatial resolution in the target region. For example, if the reconstruction matrix is too large (i.e., voxels too small), noise will increase without providing diagnostic information. At the same time, file size will become impracticably large. Such trade-offs should be optimized.

In an embodiment, a bowtie filter may be dynamically-modified in accordance with a 2D field of view map generated from acquired scout scan data. In this way, the patient model can easily be derived therefrom, with beam hardening and extra scatter effects eliminated and patient radiation exposure limited. Additionally, a field of view map may be used to perform optimal reconstructions at the smallest possible field of view that incorporates a complete patient anatomy, or of a complete patient anatomy of a region of interest.

Returning now to FIG. 2A, the simulated sinogram data generated at step 212 of sub process 110 may be used to generate, by image reconstruction, a simulated two-dimensional (2D) CT image at step 213 of sub process 110.

In an embodiment, a dose map may be generated from the simulated CT image (e.g., based on scan acquisition parameters, thereof) in order to better understand the impact of X-ray energy in different regions of the body. The dose map may be a 2D dose map, in an example. As the scan acquisition parameters, described above, are adjusted, the dose map may be updated as a reflection, thereof. In this way, the dose map allows the system to be able to effectively locate sensitive areas of the body. The X-ray beam may, therefore, be pulsed off or to a very low mA in sensitive regions (e.g., the breasts, as denoted by ovals in FIG. 2G). Moreover, since the center of the body may not be affected by a pulsed beam, if used in a standard collection method, a sparse view collection (i.e., only some views in the radial direction have X-ray on) will allow the user to decrease the dose to even the center of the body in that region.

Figure 2G:
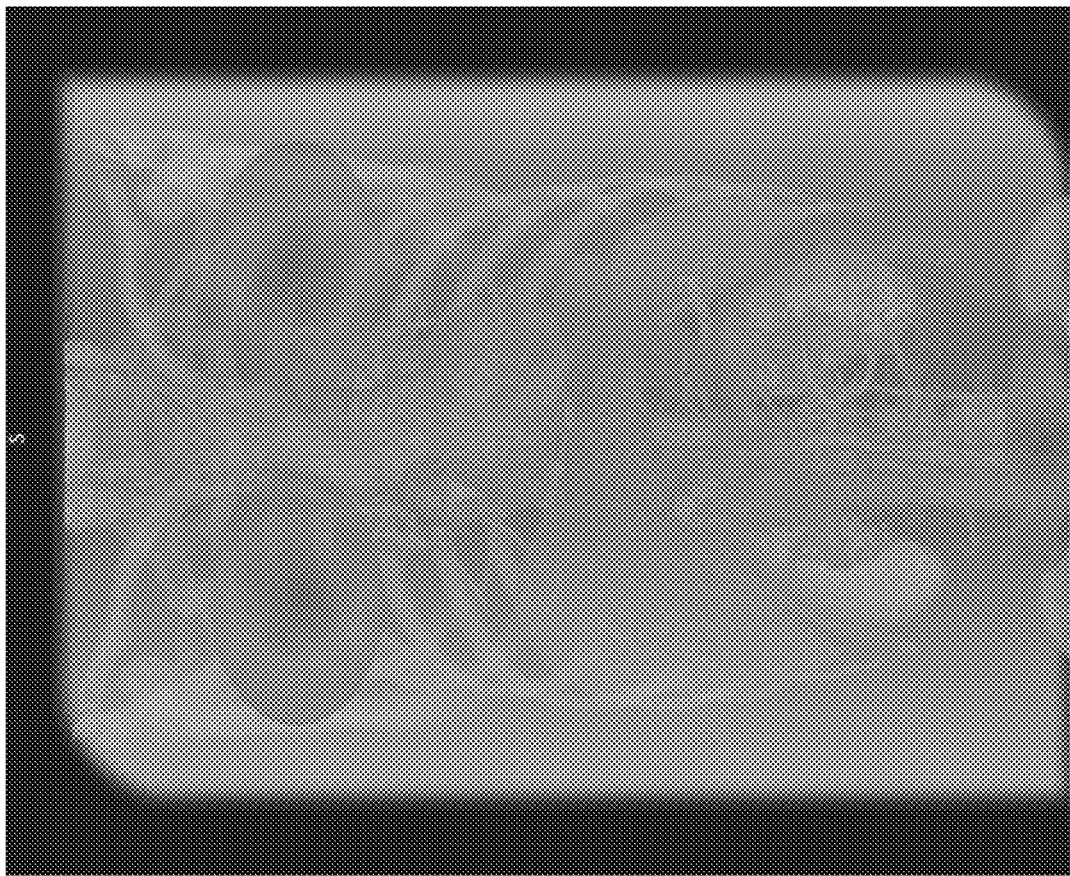
FIG. 2G is an illustration of a dose map, according to an exemplary embodiment of the present disclosure.

The dose map of FIG. 2G, and the impacts of scan acquisition parameters thereon, can be better appreciated with reference to FIG. 2H and FIG. 2I. FIG. 2H is illustrates a 2D dose map and a 2D noise map in view of a reference image, wherein the dose map and the noise map are simulated at 120 kVp and 110 mA. This can be contrasted with FIG. 2I, which illustrates a 2D dose map and a 2D noise map in view of a reference image, wherein the dose map and the noise map are simulated at 120 kVp and 400 mA. The increased tube current of FIG. 2I is evident in the simulations, where the dose maps reflect an increase in radiation exposure with increased tube current and the noise maps reflect a decrease in noise with increased tube current, as expected.

Figure 2J:
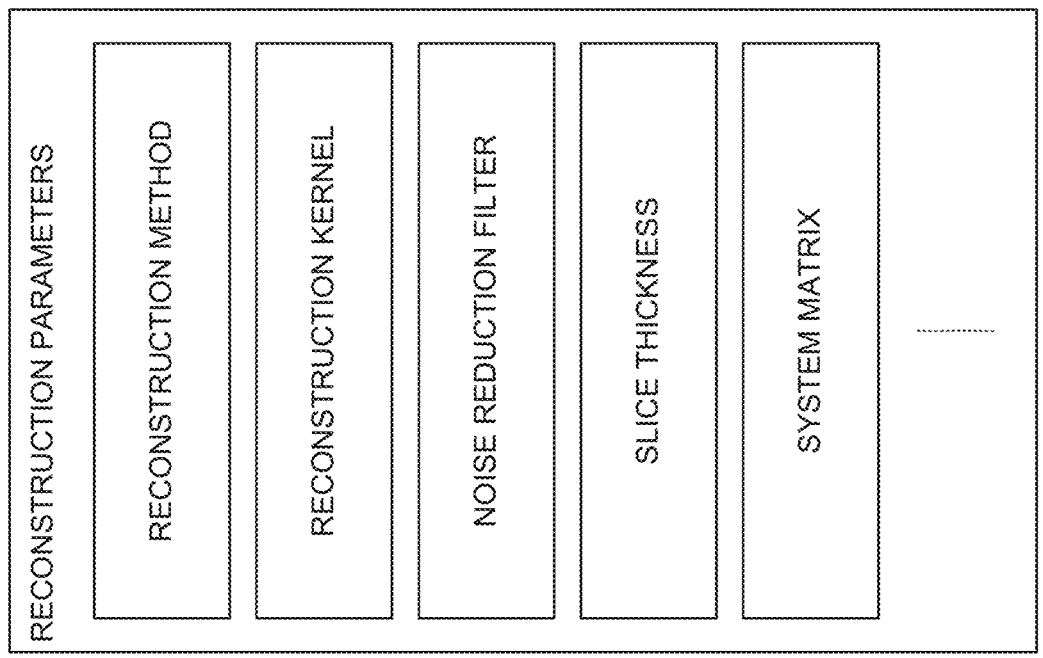
FIG. 2J is a schematic of reconstruction parameters, according to an exemplary embodiment of the present disclosure.
Figure 2L:
FIG. 2L is an illustration of an image quality map, according to an exemplary embodiment of the present disclosure.
Figure 2K:
FIG. 2K is an illustration of an image quality map, according to an exemplary embodiment of the present disclosure.

With reference to FIG. 2J, the reconstruction of the simulated 2D CT image may be performed based on a variety of image reconstruction parameters. Each of the image reconstruction parameters may be adjusted to a static variable or may be adjusted to a dynamic variable that is adjustable across a volume of a patient according to needs of the patient. For instance, each of at least one region of simulated 2D CT image of the patient may be reconstructed according to independent parameters. The image reconstruction parameters may include, among others, reconstruction method, reconstruction kernel, noise reduction filter, slice thickness, and a system matrix that simulates the scanning process. For simulation purposes, the image reconstruction parameters may be theoretical image reconstruction parameters and may be modified upon optimization of the imaging protocol. Moreover, certain parameters may be modified in different ways in order to accommodate needs of a particular patient and particular diagnostic intent. For instance, with reference to FIG. 2K and FIG. 2L, the acquired scout scan data can be used during the image reconstruction process to identify and obtain exact parameters and types of reconstruction needed in each area of the body or region of interest. In an example, the image reconstruction method may be an Advanced intelligent Clear-IQ Engine (AiCE), a Forward projected model-based Iterative Reconstruction SoluTion (FIRST), or a tomographic reconstruction, among others. The image reconstruction method may be performed on a central processing unit, graphics processing unit, or a combination thereof. The image reconstruction may be performed by one or more graphics processing units, serially or in parallel. In view of the above, it can be appreciated that areas around the heart, for instance, may require half reconstruction with parameters that differ from those of the chest or abdomen. The chest, as in FIG. 2K, may require higher spatial resolution and, therefore, may use a very sharp filter. Regions of the abdomen, as in FIG. 2L, such as the pancreas, may benefit from an increase in low-contrast resolution compared with the liver. In this way, one image reconstruction may be performed according to varying parameters in different at least one region of the patient in order to achieve improved visualization of each organ and/or region of interest of the imaging volume.

Returning now to FIG. 2A, in view of FIG. 1, the simulated 2D CT image generated at step 213 of sub process 110 and the dose map generated at step 217 of sub process 110 may be evaluated during imaging protocol optimization. The evaluation may include, in an embodiment, determining whether the scan acquisition parameters, image reconstruction parameters, and dosage are optimal. An optimization may be performed to identify the scan acquisition parameters and image reconstruction parameters that generate an image of sufficient diagnostic quality while reducing radiation exposure to the extent possible.

Determining the diagnostic quality of the image may be performed as described in the flow diagram of FIG. 3A through FIG. 3E.

Figure 3A:
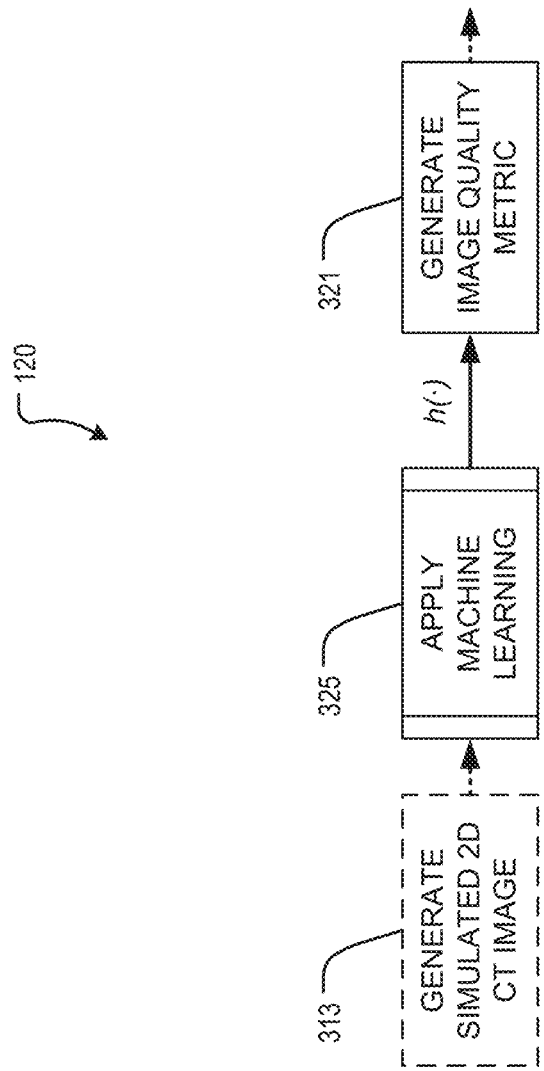
FIG. 3A is a flow diagram of a sub process of a method of generating a patient-specific imaging protocol, according to an exemplary embodiment of the present disclosure.

Referring to FIG. 3A, sub process 120 includes, at a high level, the application of machine learning to a simulated 2D CT image in order to generate a vectorized image quality assessment for at least one region of the simulated 2D CT image, wherein each of the at last one vectorized image quality assessment can be scalar-transformed to generate one or more score values, or image quality metrics, that can be evaluated against corresponding threshold score values for each region and, ultimately, used to determine if a theoretical full CT scan based on the simulated CT scan acquisition parameters and image reconstruction parameters would be of diagnostic value.

To this end, machine learning may be applied at sub process 325 of sub process 120 to a simulated 2D CT image generated at step 313. Application of the machine learning, which may include application of an artificial neural network, allows for the generation of one or more assessment values that are representative of the image quality. The one or more assessment values, as described later, may be included within an at least one probabilistic quality representation generated by the artificial neural network for each of at least one region. The at least one probabilistic quality representation, once transformed to a scalar value, may be used as a score value for subsequent evaluation of each of the at least one region in view of dose maps.

According to an embodiment, the one or more assessment values for each of at least one region, which define an at least one probabilistic quality representation (PQR), may be based on physician assessments of training images upon which the artificial neural network has been trained. As discussed, the artificial neural network may be one selected from a group of artificial neural networks trained based upon hypothetical patient populations. For instance, the artificial neural network may be one trained to evaluate specific regions of interest, diseases of interest, and the like. In this way, the artificial neural network is tailored to value certain image attributes more or less than other image attributes based on the specific region of interest and/or disease being evaluated and in view of diagnostic value, as indicated by clinician assessment of image quality.

According to an embodiment, each customized artificial neural network may be trained according to training images scored by clinicians. In an embodiment, a scoring clinician may assign assessment values to at least one region of each training image. In this way, the one or more artificial neural networks capture the differences between image quality needs of the skull and the abdomen, as an example, within a single image or across multiple images. Moreover, as it relates to a combination of region specificity and disease specificity, such an approach accounts for the understanding that a chest X-ray for a patient with lung disease may require different image quality attributes from a chest X-ray for a patient with a rib fracture. By acknowledging the diagnostic variability of certain image quality attributes, as prescribed by assessing clinicans, each customized artificial neural network provides a tailored estimation of image quality attributes relevant to specific needs of a patient.

Figure 3B:
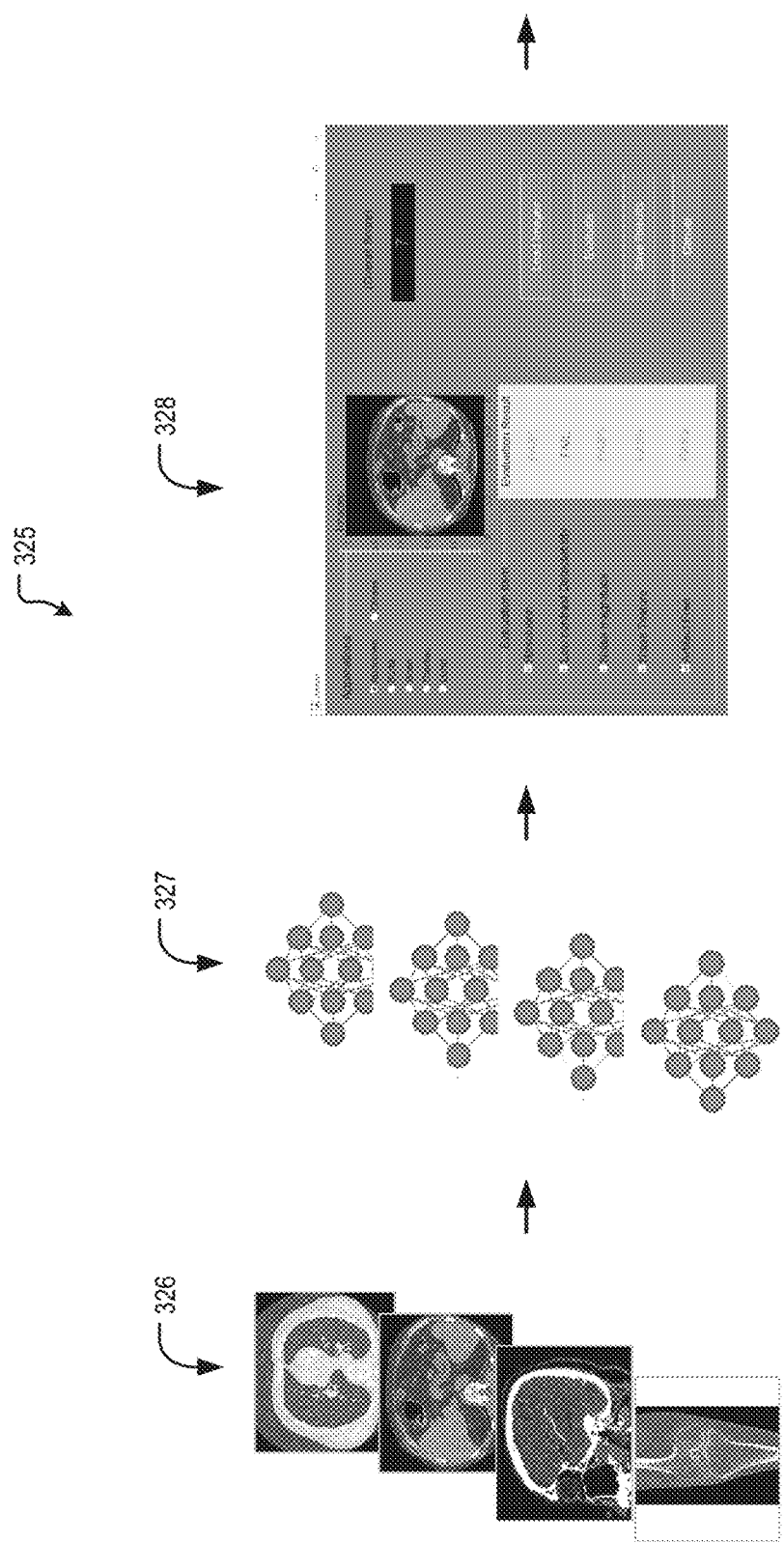
FIG. 3B is an illustration of a flow diagram of a sub process of a method of generating a patient-specific imaging protocol, according to an exemplary embodiment of the present disclosure.

Turning now to FIG. 3B, a high-level illustration of a flow diagram of the applied machine learning is provided. At step 326 of sub process 325, a simulated 2D CT image may be provided. In an embodiment, certain features of the simulated 2D CT image may be known, including the region of interest. The known features may include other factors, in addition to the region of interest, such as patient demographics. A corresponding neural network may then be selected at step 327 of sub process 325 based on the known features, the corresponding neural network being selected based on the patient being imaged. The corresponding neural network at step 327 of sub process 325 may be configured to, as described above, value certain image attributes more/less than other image attributes when generating an image quality assessment at step 328 of sub process 325. The image quality assessment at step 328 of sub process 325 may be a blind quality image assessment. The image quality assessment at step 328 of sub process 325 includes the generation of values related to, in an example, 'resolution', 'low contrast detectability', 'noise magnitude', 'noise texture', and 'artifact free'. The generated values may be generated for at least one region of the simulated 2D CT image In an embodiment, each output of the image quality assessment at step 328 of sub process 325 may be a PQR reflecting one or more of the individual image quality assessment values.

Figure 3C:
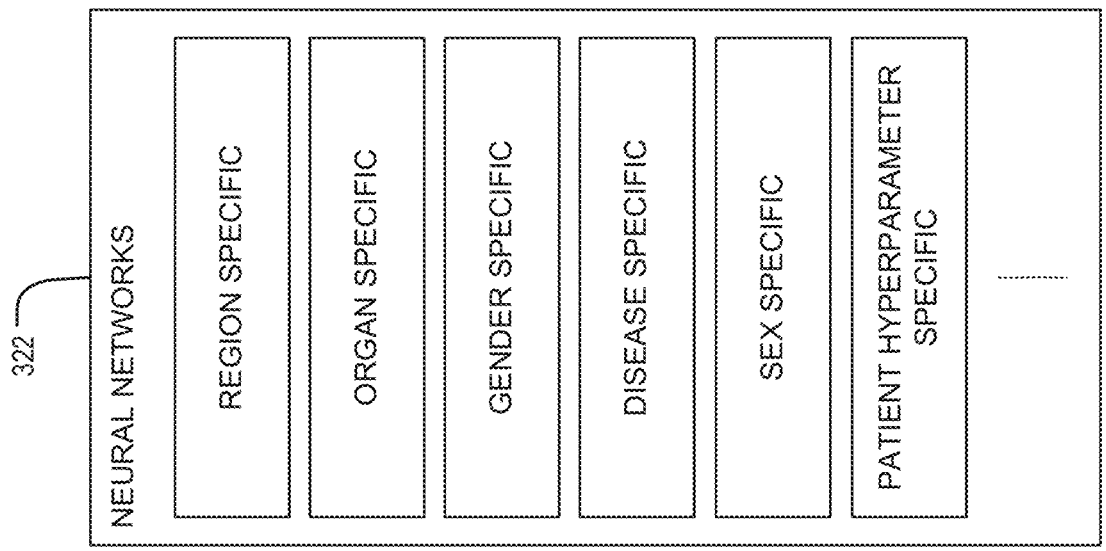
FIG. 3C is a flow diagram of a sub process of a method of generating a patient-specific imaging protocol, according to an exemplary embodiment of the present disclosure.

The corresponding neural network selected at step 327 of sub process 325 may be further appreciated in view of FIG. 3C. FIG. 3C is a schematic demonstrating a variety of factors 322 that may, in combination or individually, define the training of a neural network. The factors 322 may include region of interest, organ of interest, gender, and disease, and may result in neural networks that are, individually, region-specific, organ-specific, gender-specific, disease-specific, and the like. Further, this may include neural networks that are sex-specific and patient hyperparameter-specific, patient hyperparameters including, as examples, body shape and size (i.e. body mass index and weight). Of course, the above should be considered a non-limiting set of tailored neural networks and any additional, affecting factors may be accommodated within a neural network. Moreover, a neural network may be trained to favor a combination of the factors 322 in accordance with the preferences of a plurality of clinicians that provide image quality assessments.

Figure 3D:
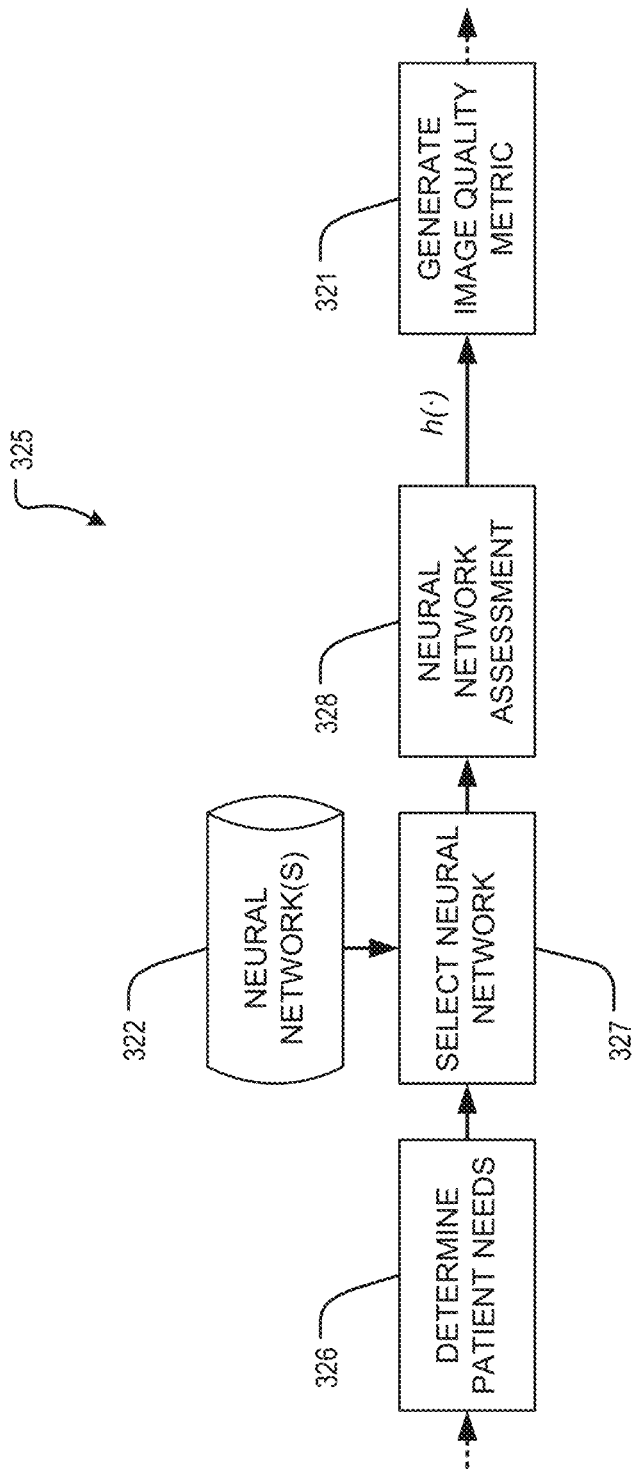
FIG. 3D is a schematic of a variables a neural network may be tailored for, according to an exemplary embodiment of the present disclosure.

The illustration of the flow diagram of FIG. 3B, including step 329 of sub process 325, will now be described with reference to the flow diagram of FIG. 3D.

At step 326 of sub process 325, patient needs may be determined. This can include input from a clinician regarding the application, task, gender, and region, among others, pertinent to the patient. Based on the patient needs determined at step 326 of sub process 325, an appropriate neural network can be selected at step 327 of sub process 325 based on a neural network database available at step 322 of sub process 325. The selected neural network provides a neural network trained to evaluate a specific type of patient in view of image quality attributes deemed important by assessing physicians. At step 328 of sub process 325, the selected neural network may be applied to a simulated 2D CT image and an image quality assessment may be generated for each of at least one region of the simulated 2D CT image as one or more PQRs. The one or more PQRs, as the image quality assessment, may assess overall quality in addition to resolution, low contrast detectability, noise magnitude, noise texture, and artifacts. As would be understood by one of ordinary skill in the art, the generated one or more PQRs are vectors capturing each of one or more image quality attributes that comprise it. In order to provide a scalar form of the generated one or more PQRs, the vectorized PQRs must be transformed at step 321 of sub process 325 in order to generate corresponding image quality metrics, or score values.

Having generated the one or more image quality metrics for a given simulated image, an evaluation of the simulated image in view of a corresponding dose map may be performed.

The evaluation may be an optimization of the scan acquisition parameters and the image reconstruction parameters for each of the at least one region of the simulated image in order to maximize corresponding score values while minimizing radiation exposure to the patient.

Figure 4:
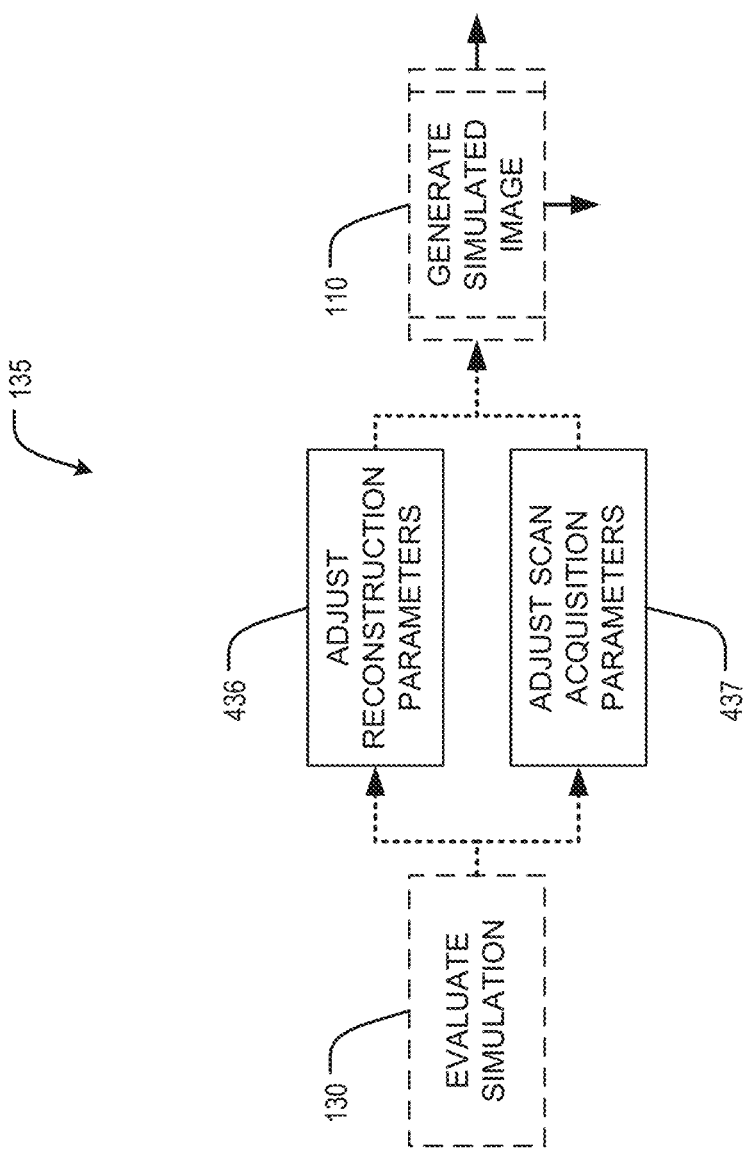
FIG. 4 is a flow diagram of a sub process of a method of generating a patient-specific imaging protocol, according to an exemplary embodiment of the present disclosure.

To this end, FIG. 4 describes sub process 135 of method 100, wherein image reconstruction parameters and scan acquisition parameters may be adjusted for each of at least one region of the simulated image in view of determined image quality and radiation exposure. Having negatively evaluated the simulation at step 130 of sub process 135, the scan acquisition parameters may be adjusted at step 437 of sub process 135 and the image reconstruction parameters may be adjusted at step 436 of sub process 135. Having performed initial adjustments to the scan acquisition parameters and the image reconstruction parameters, an image can be iteratively simulated at sub process 110 of method 100. Two lines lead away from sub process 110 of method 100 to indicate that, concurrently, the simulated image may be evaluated for image quality and may be used to generate a dose map used during a subsequent evaluation. Of course, the optimization of sub process 135 of method 100 may be iteratively performed until conditions are satisfied at step 130 of method 100 and the scan acquisition parameters and image reconstruction parameters are deemed appropriate for implementation within a full CT scan.

Figure 5:
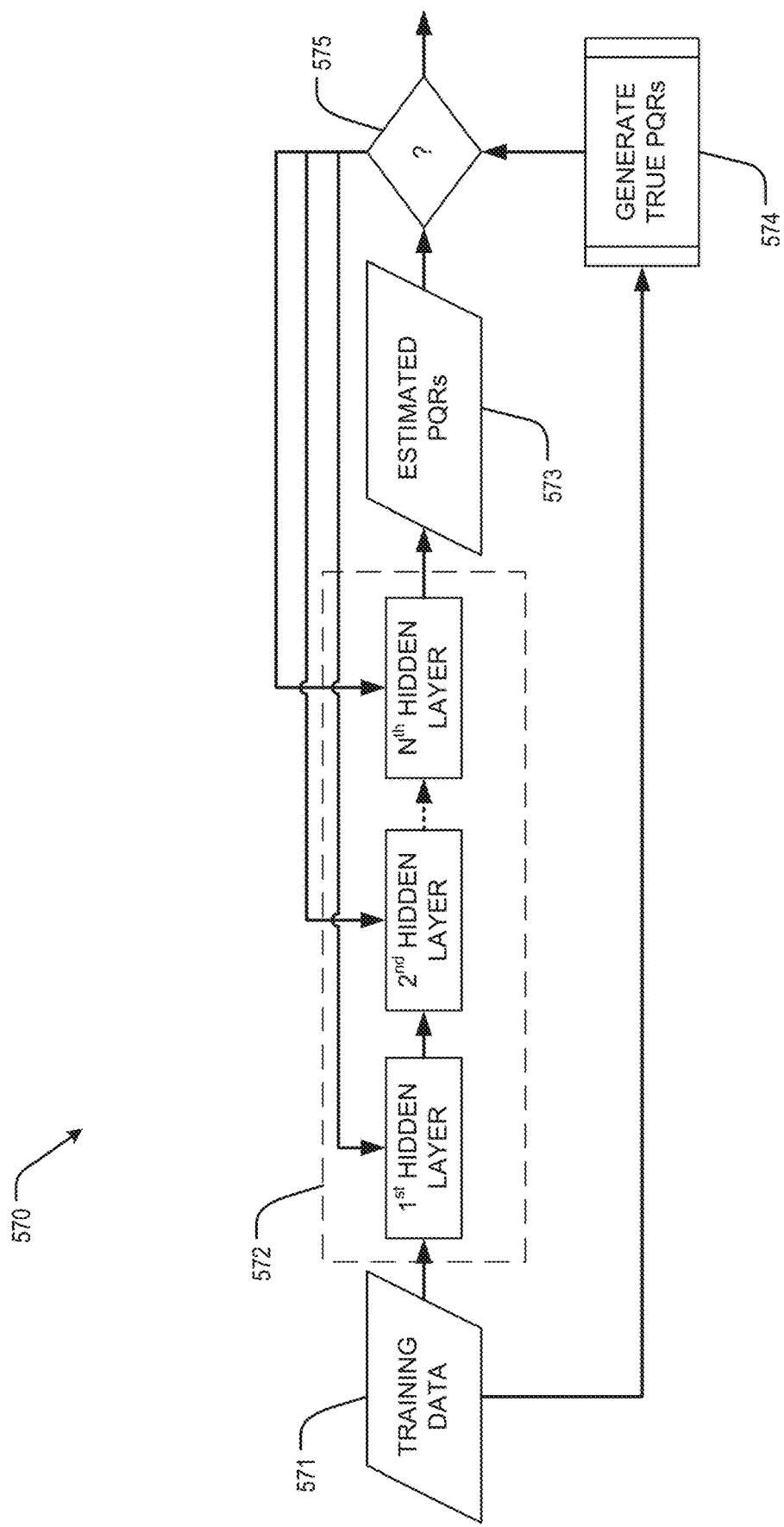
FIG. 5 is a flow diagram of a training process of a neural network, according to an exemplary embodiment of the present disclosure.

FIG. 5 shows a flow diagram of process 570 describing training and optimization of, as the artificial neural network, a convolutional neural network (CNN), according to an exemplary embodiment of the present disclosure. The type of artificial neural network used can vary with application and can include residual networks, convolutional neural networks and encoder/decoder networks, among others. During training, the CNN receives training data, or, for instance, a scout scan, as an input and outputs one or more PQRs that are minimized relative to a reference, or 'true PQRs'. The generated 'true PQRs' may be based on ground-truth data or, for instance, physician input regarding image quality.

Specifically, training the CNN begins with providing the training data as an input layer at step 571. The input layer at step 571 can undergo convolution by a filter of a predefined size and activation. In an exemplary embodiment, the activation is a rectified linear unit (ReLU). The output of the input layer, or feature map, is then the input of a first hidden layer of n hidden layers 572. At the first hidden layer, the feature map is further modified via, for example, convolution, batch normalization, and activation by ReLU. In an embodiment, the output feature map of the first hidden layer is then the input feature map for a second hidden layer. The second hidden layer can be a pooling layer, for example, downsampling the feature map to improve computational speed. Subsequent n hidden layers 572 of the network can be included, as needed. The output of an $n^{th}$ hidden layer then becomes the input for an output layer at step 573, the output layer at step 573 being a fully connected layer and describing one or more estimated PQRs for the training data. The CNN PQR estimation from the output layer at step 573 can then be compared with the concurrently generated 'true PQRs', or reference PQRs, at sub process 574, and a loss function can be minimized therebetween. In an embodiment, the estimated PQRs and the 'true PQRs' may populate an estimated PQR matrix and a true PQR matrix, wherein each matrix describes a visual map that includes PQR values for each of at least one region within the simulated image. Accordingly, the loss function may evaluate an estimated PQR matrix and a true PQR matrix. If, at step 575, it is determined that a criterion is met and the loss function has been minimized (i.e., there is an acceptable difference between the estimated PQR matrix and the true PQR matrix), the CNN is sufficiently trained and is ready for implementation with uncorrected data. Alternatively, if it is determined at step 575 that the criterion is not met and the loss function has not been minimized, the process returns to the input layer at step 571 and updates are made to weights/coefficients of the n hidden layers 572 of the neural network.

According to an embodiment, as implemented at step 575 of FIG. 5, the loss function can be simply defined by the mean square error between a CNN-estimated PQR matrix ($PQR_{CNN}$), or estimated PQR matrix, and generated 'true PQR' matrix ($PQR_{true}$), or true PQR matrix. In other words, $$\frac{1}{n}\sum_{i=1}^{n}(PQR_{true} - PQR_{CNN})^2$$

where n is the number for the training data. In an example, the loss function can be minimized using classic deep learning optimization methods, such as stochastic gradient descent, among others. The above-described loss function will be described with detail in a later section.

Further to the pooling layers of the above-described CNN, computational energy can be conserved through sparse-view training, as scatter change between views are often slow. Therefore, sparse-view training can be used to reduce the training time. Moreover, down-sampling for each view can further reduce the training size, conserving training time and testing time.

Now, a more detailed description of FIG. 5 is provided. This description can be generalized, as would be understood by one of ordinary skill in the art.

Figure 6:
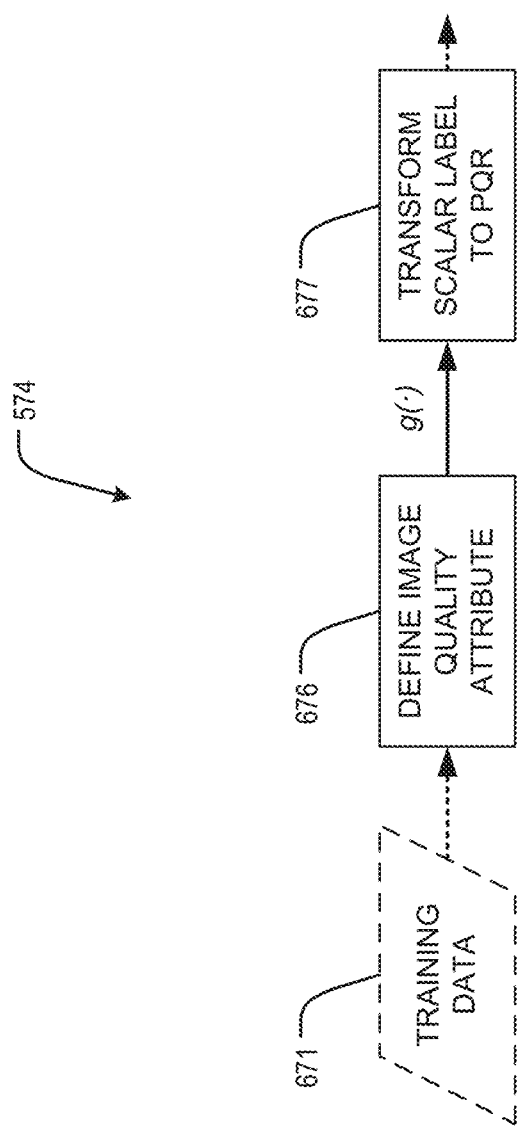
FIG. 6 is a flow diagram of a sub process of a training process of a neural network, according to an exemplary embodiment of the present disclosure.

With reference to FIG. 6, the 'true PQRs' used for minimization of the estimated PQR matrix may be generated at sub process 574 of method 570. In an embodiment, for a given set of training datasets $\{x_n, y_n\}$, n=1, ... N, acquired from training data at step 671, image quality attributes of a given image may be defined as a set of "quality anchors" lying within the range of scores $\{c_m\}$, m=1, ... M at step 676 of sub process 574. In an embodiment, each of the "quality anchors" for at least one region of a given training image may be assigned a value. At step 677 of sub process 574, the value, or an image quality assessment value, of each "quality anchor" can be transformed into a PQR via transformation function g(•) at step 677 of sub process 574. During training, estimation of PQRs of the at least one region, which form an estimated PQR matrix, is sufficient for evaluation between the CNN under training and the generated 'true PQRs' matrix. It can be appreciated, however, that each PQR value of the estimated PQR matrix must be transformed by a function h(•) back to a scalar score during implementation of the CNN so that it may be used during evaluation of the simulated CT image and corresponding dose map. For the sake of brevity, a detailed description of implementation of a PQR matrix is excluded. An implementation of a PQR matrix, similar to that which is employed in the present disclosure, can be appreciated with reference to "A Probabilistic Quality Representation Approach to Deep Blind Image Quality Prediction" by Zeng et al.

Figure 7:
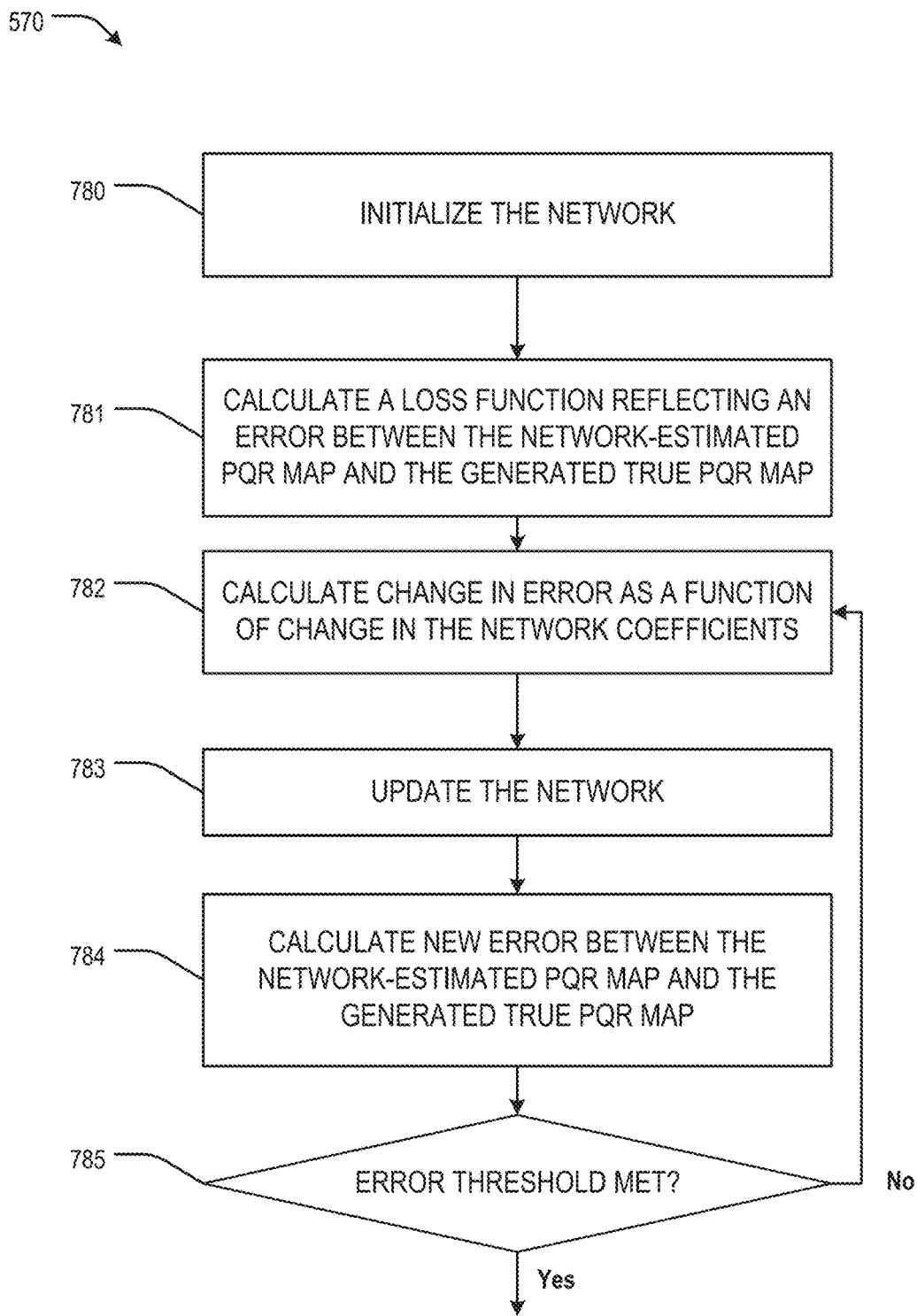
FIG. 7 is a flow diagram of training of a neural network, according to an exemplary embodiment of the present disclosure.

FIG. 7 shows a flow diagram of one implementation of the training 570 performed during the PQR estimation method. In process 570 of the method, representative data from the training data database are used as training data to train a CNN, resulting in the CNN being output from step 785. The term "data" here can refer to an image of the training image database. In an example using training images for data, the offline training method of process 570 trains the CNN using a large number of training images, which may be CT medical images generally reflective a wide variety of patients, conditions, and body regions, or may be specifically-tailored to specific patients, conditions, and body regions, that are paired with corresponding 'labeled' training images to train the CNN to estimate PQR scores from the training images.

In process 570, a training database is accessed to obtain a plurality of datasets and the network is iteratively updated to reduce the error (e.g., the value produced by a loss function), wherein updating the network includes iteratively updating values of, for example, network coefficients, at each layer of the CNN, such that the data processed by the CNN, increasingly, matches the 'true PQR' matrix generated by the reference data. In other words, CNN infers the mapping implied by the training data, and the cost function produces an error value related to the mismatch between the data from the ground-truth data and the estimated PQR matrix output of the current iteration of the CNN. For example, in certain implementations, the cost function can use the mean-square error to minimize the average squared error. In the case of a multilayer perceptron (MLP) neural network, the backpropagation algorithm can be used for training the network by minimizing the mean-square-error-based cost function using a (stochastic) gradient descent method. A more-detailed discussion of updating of network coefficients can be found below with reference to FIG. 8.

Training a neural network model essentially means selecting one model from the set of allowed models (or, in a Bayesian framework, determining a distribution over the set of allowed models) that minimizes the cost criterion (i.e., the error value calculated using the cost function). Generally, the CNN can be trained using any of numerous algorithms for training neural network models (e.g., by applying optimization theory and statistical estimation).

For example, the optimization method used in training the CNN can use a form of gradient descent incorporating backpropagation to compute the actual gradients. This is done by taking the derivative of the cost function with respect to the network parameters and then changing those parameters in a gradient-related direction. The backpropagation training algorithm can be: a steepest descent method (e.g., with variable learning rate, with variable learning rate and momentum, and resilient backpropagation), a quasi-Newton method (e.g., Broyden-Fletcher-Goldfarb-Shanno, one step secant, and Levenberg-Marquardt), or a conjugate gradient method (e.g., Fletcher-Reeves update, Polak-Ribiere update, Powell-Beale restart, and scaled conjugate gradient). Additionally, evolutionary methods, such as gene expression programming, simulated annealing, expectation-maximization, non-parametric methods and particle swarm optimization, can also be used for training the CNN.

With reference again to FIG. 7, the flow diagram is a non-limiting example of an implementation of training process 570 for training the CNN using the training data. The data in the training data can be from any of the training datasets within the training database.

In step 780 of process 570, an initial guess is generated for the coefficients of the CNN. For example, the initial guess can be based on a priori knowledge of the region being imaged or one or more exemplary denoising methods, edge-detection methods, and/or blob detection methods. Additionally, the initial guess can be based on one of the LeCun initialization, an Xavier initialization, and a Kaiming initialization.

Step 781 to step 785 provides a non-limiting example of an optimization method for training the CNN. In step 781 of process 570, an error is calculated (e.g., using a loss function or a cost function) to represent a measure of the difference (e.g., a distance measure) between a matrix, or map, of the 'true' generated data (i.e., physician labeling-based 'true PQR', ground truth data) and a matrix, or map, of the output data of the CNN as applied in a current iteration of the CNN. The error can be calculated using any known cost function or distance measure between the image data, including those cost functions described above. Further, in certain implementations the error/loss function can be calculated using one or more of a hinge loss and a cross-entropy loss. In an example, as described above, the loss function can be defined as the mean square error between the output of the CNN ($PQR_{CNN}$) and the generated 'true PQR' data ($PQR_{true}$), or $$\frac{1}{n}\sum_{i=1}^{n}(PQR_{true} - PQR_{CNN})^2$$

where n is the number for the training object. As described above, this loss can be minimized using optimization methods including, among others, stochastic gradient descent.

Additionally, the loss function can be combined with a regularization approach to avoid overfitting the network to the particular instances represented in the training data. Regularization can help to prevent overfitting in machine learning problems. If trained too long, and assuming the model has enough representational power, the network will learn the features specific to that dataset, which is referred to as overfitting. In case of overfitting, the CNN becomes a poor generalization, and the variance will be large because the features vary between datasets. The minimum total error occurs when the sum of bias and variance are minimal. Accordingly, it is desirable to reach a local minimum that explains the data in the simplest possible way to maximize the likelihood that the trained network represents a general solution, rather than a solution particular to the features in the training data. This goal can be achieved by, for example, early stopping, weight regularization, lasso regularization, ridge regularization, or elastic net regularization.

In certain implements the CNN is trained using backpropagation. Backpropagation can be used for training neural networks and is used in conjunction with gradient descent optimization methods. During a forward pass, the algorithm computes the network's prediction matrix based on the current parameters, which may be, for instance, weights/coefficients. The PQR prediction matrix can then be input into the loss function, by which it is compared to a corresponding ground truth label matrix (i.e., physician label-based 'true PQR'). During the backward pass, the model computes the gradient of the loss function with respect to the current parameters, after which the parameters are updated by taking a step size of a predefined size in the direction of minimized loss (e.g., in accelerated methods, such that the Nesterov momentum method and various adaptive methods, the step size can be selected to more quickly converge to optimize the loss function.

The optimization method by which the backprojection is performed can use one or more of gradient descent, batch gradient descent, stochastic gradient descent, and mini-batch stochastic gradient descent. Additionally, the optimization method can be accelerated using one or more momentum update techniques in the optimization approach that results in faster convergence rates of stochastic gradient descent in deep networks, including, e.g., Nesterov momentum technique or an adaptive method, such as Adagrad sub-gradient method, an Adadelta or RMSProp parameter update variation of the Adagrad method, and an Adam adaptive optimization technique. The optimization method can also apply a second order method by incorporating the Jacobian matrix into the update step.

The forward and backward passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to the non-limiting example shown in FIG. 7, step 782 of process 570 determines a change in the error as a function of the change in the network can be calculated (e.g., an error gradient) and this change in the error can be used to select a direction and step size for a subsequent change in the weights/coefficients of the CNN. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 783 of process 570, a new set of coefficients are determined for the CNN. For example, the weights/coefficients can be updated using the change calculated in step 782, as in a gradient descent optimization method or an over-relaxation acceleration method.

In step 784 of process 570, a new error value is calculated using the updated weights/coefficients of the CNN.

In step 785 of process 570, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations are reached. When the stopping criteria is not satisfied the training process performed in process 570 will continue back to the start of the iterative loop by returning and repeating step 782 using the new weights and coefficients (the iterative loop includes steps 782, 783, 784, and 785). When the stopping criteria are satisfied, the training process performed in process 570 is completed.

Figure 8:
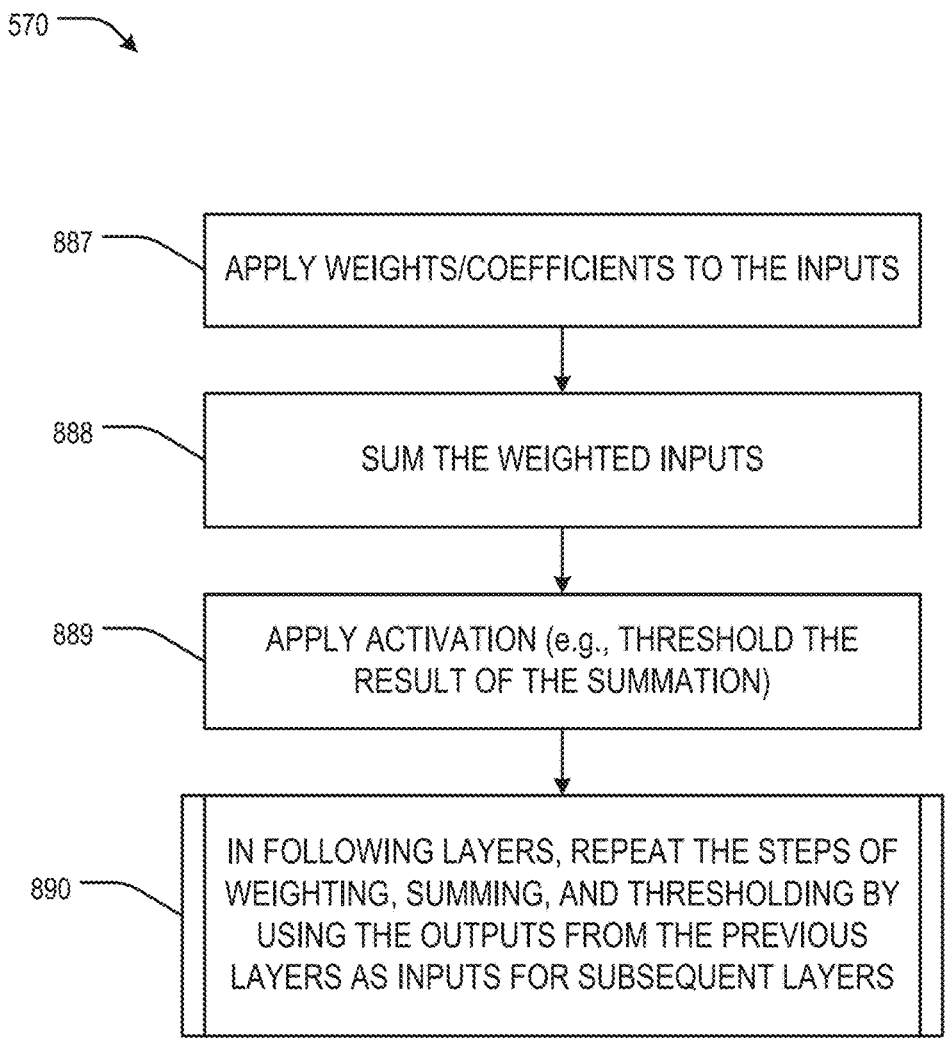
FIG. 8 is a generalized flow diagram of implementation of an artificial neural network, according to an exemplary embodiment of the present disclosure.
Figure 9:
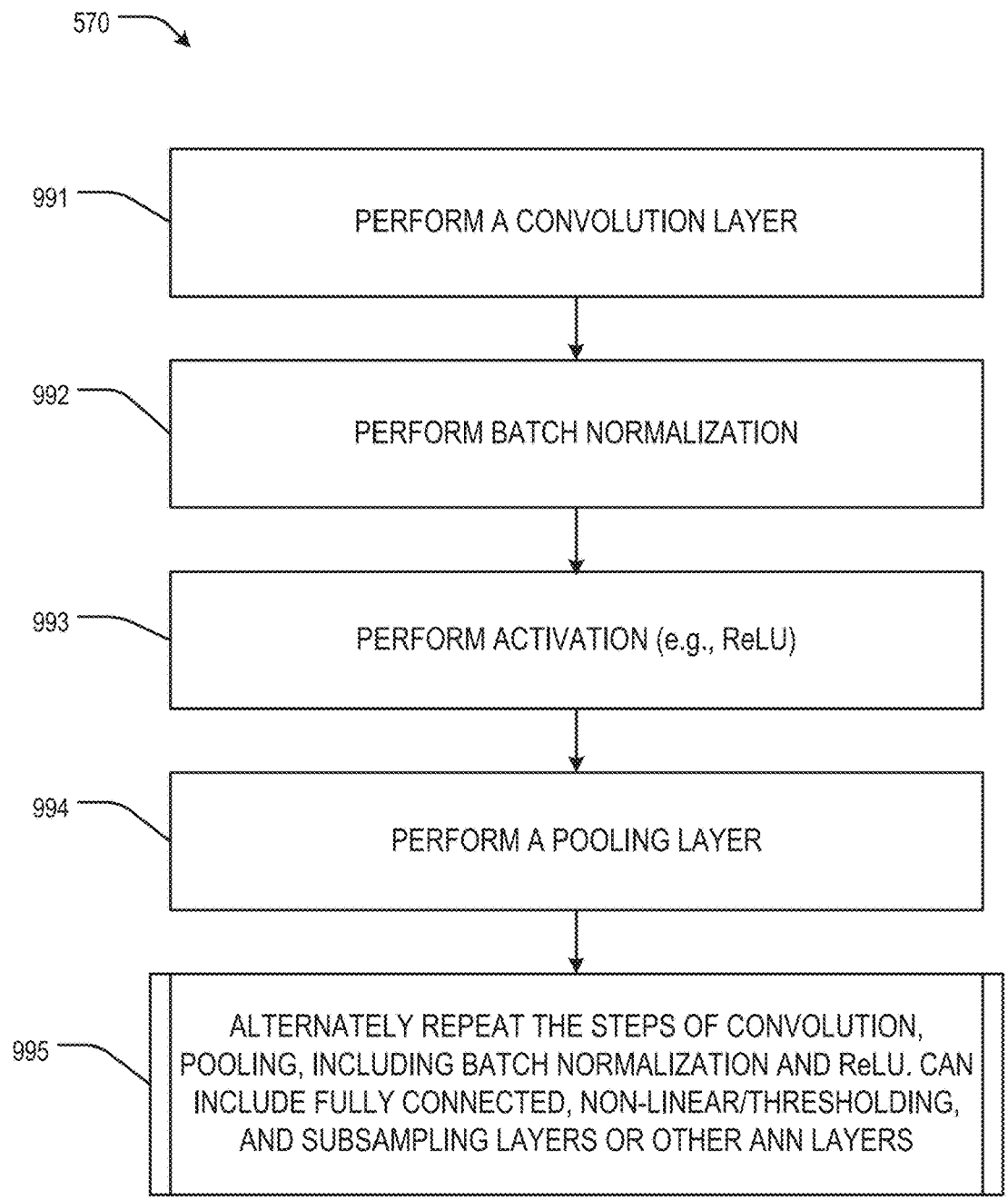
FIG. 9 is a flow diagram of implementation of a convolutional neural network, according to an exemplary embodiment of the present disclosure.

FIG. 8 and FIG. 9 show flow diagrams of implementations of process 570. FIG. 8 is general for any type of layer in a feedforward artificial neural network (ANN), including, for example, fully connected layers, whereas FIG. 9 is specific to convolutional, pooling, batch normalization, and ReLU layers in a CNN. The CNN of the present disclosure can include both fully connected layers and convolutional, pooling, batch normalization, and ReLU layers, resulting in a flow diagram that is a combination of FIG. 8 and FIG. 9, as would be understood by one of ordinary skill in the art. The implementations of process 570 shown in FIG. 8 and FIG. 9 also correspond to applying the CNN to the respective data, or training images, of the training dataset.

In step 887, the weights/coefficients corresponding to the connections between neurons (i.e., nodes) are applied to the respective inputs corresponding to, for example, the pixels of the training image.

In step 888, the weighted inputs are summed. When the only non-zero weights/coefficients connecting to a given neuron on the next layer are regionally localized in an image represented in the previous layer, the combination of step 887 and step 888 is essentially identical to performing a convolution operation.

In step 889, respective thresholds are applied to the weighted sums of the respective neurons.

In process 890, the steps of weighting, summing, and thresholding are repeated for each of the subsequent layers.

FIG. 9 shows a flow diagram of another implementation of process 570. The implementation of process 570 shown in FIG. 9 corresponds to operating on the training image at a hidden layer using a non-limiting implementation of the CNN.

In step 991, the calculations for a convolution layer are performed as discussed in the foregoing and in accordance with the understanding of convolution layers of one of ordinary skill in the art.

In step 992, following convolution, batch normalization can be performed to control for variation in the output of the previous layer, as would be understood by one of ordinary skill in the art.

In step 993, following batch normalization, activation is performed according to the foregoing description of activation and in accordance with the understanding of activation of one of ordinary skill in the art. In an example, the activation function is a rectified activation function or, for example, a ReLU, as discussed above.

In another implementation, the ReLU layer of step 993 may be performed prior to the batch normalization layer of step 992.

In step 994, the outputs from the convolution layer, following batch normalization and activation, are the inputs into a pooling layer that is performed according to the foregoing description of pooling layers and in accordance with the understanding of pooling layers of one of ordinary skill in the art.

In process 995, the steps of a convolution layer, pooling layer, batch normalization layer, and ReLU layer can be repeated in whole or in part for a predefined number of layers.

Following (or intermixed with) the above-described layers, the output from the ReLU layer can be fed to a predefined number of ANN layers that are performed according to the description provided for the ANN Layers in FIG. 8. The final output will be scatter estimation.

Figure 10A:
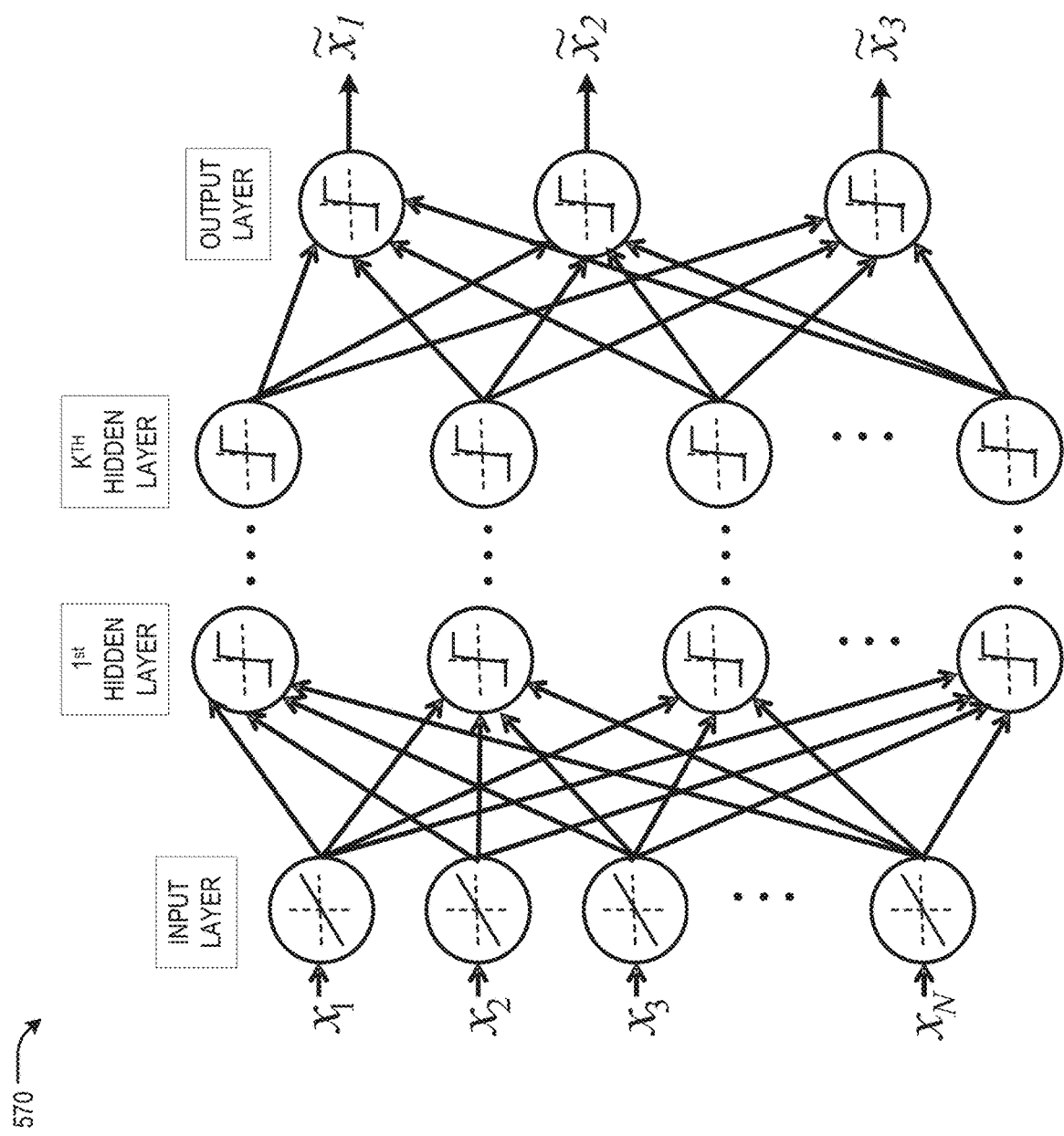
FIG. 10A is an example of a feedforward artificial neural network.
Figure 10B:
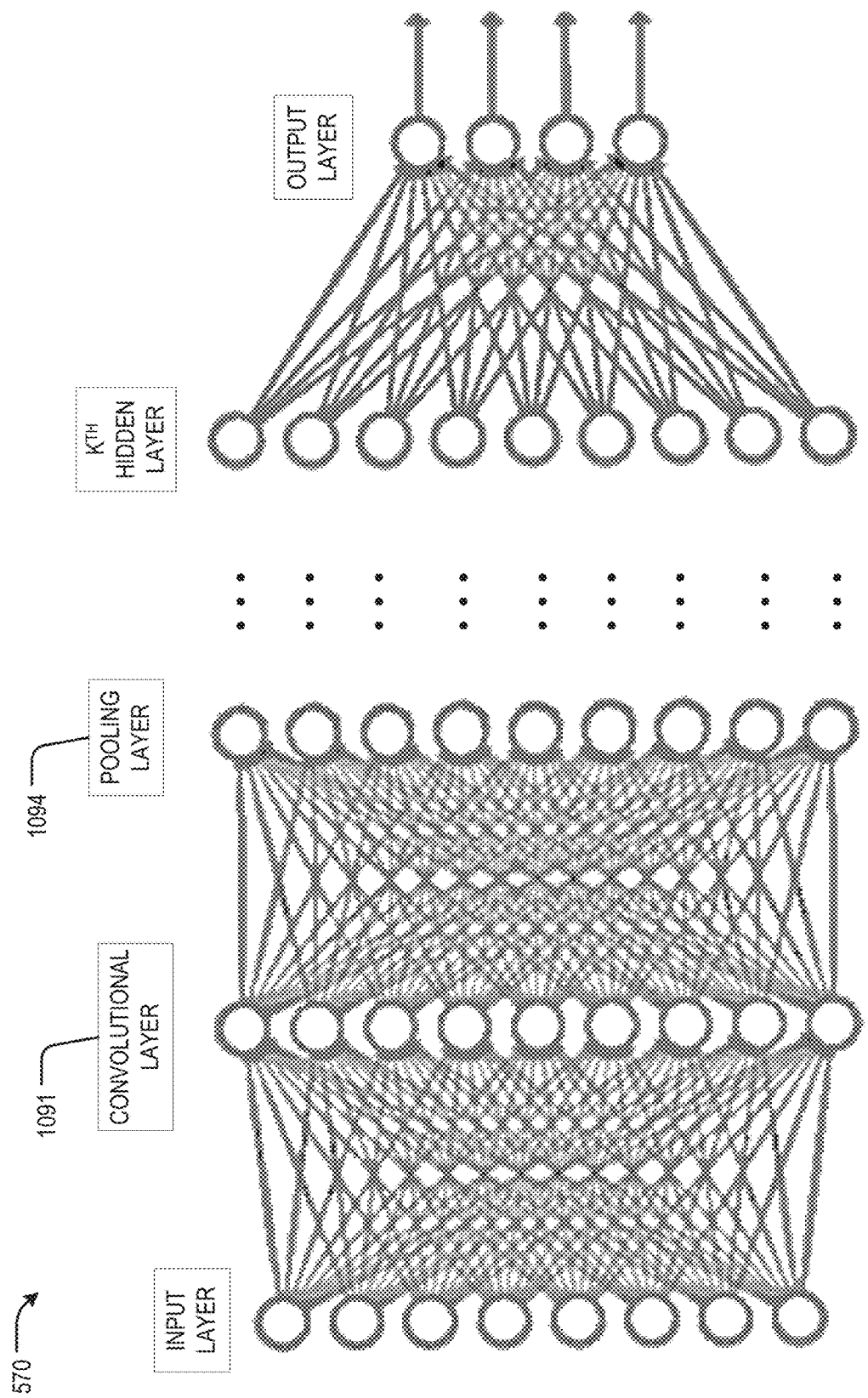
FIG. 10B is an example of a convolutional neural network, according to an exemplary embodiment of the present disclosure.

FIG. 10A and FIG. 10B show examples of the interconnections between layers in the CNN network. The CNN can include fully connected, convolutional, pooling, batch normalization, and activation layers, all of which are explained above and below. In certain preferred implementations of the CNN, convolutional layers are placed close to the input layer, whereas fully connected layers, which perform the high-level reasoning, are placed further down the architecture towards the loss function. Pooling layers can be inserted after convolutions and provide a reduction lowering the spatial extent of the filters, and thus the amount of learnable parameters. Batch normalization layers regulate gradient distractions to outliers and accelerate the learning process. Activation functions are also incorporated into various layers to introduce nonlinearity and enable the network to learn complex predictive relationships. The activation function can be a saturating activation function (e.g., a sigmoid or hyperbolic tangent activation function) or rectified activation function (e.g., ReLU discussed above).

FIG. 10A shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The simplest ANN has three layers and is called an autoencoder. The CNN of the present disclosure can have more than three layers of neurons and have as many output neurons $\tilde{x}_N$ as input neurons, wherein N is the number of, for example, pixels in the training image. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m(x) is defined as a composition of other functions $n_i(x)$, which can be further defined as a composition of other functions. This can be conveniently represented as a network structure, with arrows depicting the dependencies between variables, as shown in FIG. 10A and FIG. 10B. For example, the ANN can use a nonlinear weighted sum, wherein $m(x)=K(\Sigma_i w_i n_i(x))$ and where K (commonly referred to as the activation function) is some predefined function, such as the hyperbolic tangent.

In FIG. 10A (and similarly in FIG. 10B), the neurons (i.e., nodes) are depicted by circles around a threshold function. For the non-limiting example shown in FIG. 10A, the inputs are depicted as circles around a linear function and the arrows indicate directed communications between neurons. In certain implementations, the CNN is a feedforward network.

The CNN of the present disclosure operates to achieve a specific task, such as estimating a PQR matrix of a simulated CT image, by searching within the class of functions F to learn, using a set of observations, to find $m^* \in F$, which solves the specific task in some optimal sense (e.g., the stopping criteria used in step 885 discussed above). For example, in certain implementations, this can be achieved by defining a cost function $C: F \to m$ such that, for the optimal solution m*, C(m*)≤C(m)∀m∈F (i.e., no solution has a cost less than the cost of the optimal solution). The cost function C is a measure of how far away a particular solution is from an optimal solution to the problem to be solved (e.g., the error). Learning algorithms iteratively search through the solution space to find a function that has the smallest possible cost. In certain implementations, the cost is minimized over a sample of the data (i.e., the training data).

FIG. 10B shows a non-limiting example of a convolutional neural network (CNN), as in the present disclosure. CNNs are a type of ANN that have beneficial properties for image processing and, therefore, have special relevancy for applications of image processing. CNNs use feedforward ANNs in which the connectivity pattern between neurons can represent convolutions in image processing. For example, CNNs can be used for image-processing optimization by using multiple layers of small neuron collections which process portions of the input image, called receptive fields. The outputs of these collections can then be tiled so that they overlap to obtain a better representation of the original image. This processing pattern can be repeated over multiple layers having convolution 1091 and pooling layers 1094, as shown, and can include batch normalization and activation layers.

As generally applied above, following after a convolution layer 1091, a CNN can include local and/or global pooling layers 1094 which combine the outputs of neuron clusters in the convolution layers. Additionally, in certain implementations, the CNN can also include various combinations of convolutional and fully connected layers, with pointwise nonlinearity applied at the end of or after each layer.

CNNs have several advantages for image processing. To reduce the number of free parameters and improve generalization, a convolution operation on small regions of input is introduced. One significant advantage of certain implementations of CNNs is the use of shared weight in convolution layers, which means that the same filter (weights bank) is used as the coefficients for each pixel in the layer, both reducing memory footprint and improving performance. Compared to other image processing methods, CNNs advantageously use relatively little pre-processing. This means that the network is responsible for learning the filters that in traditional algorithms were hand-engineered. The lack of dependence on prior knowledge and human effort in designing features is a major advantage for CNNs.

Figure 11:
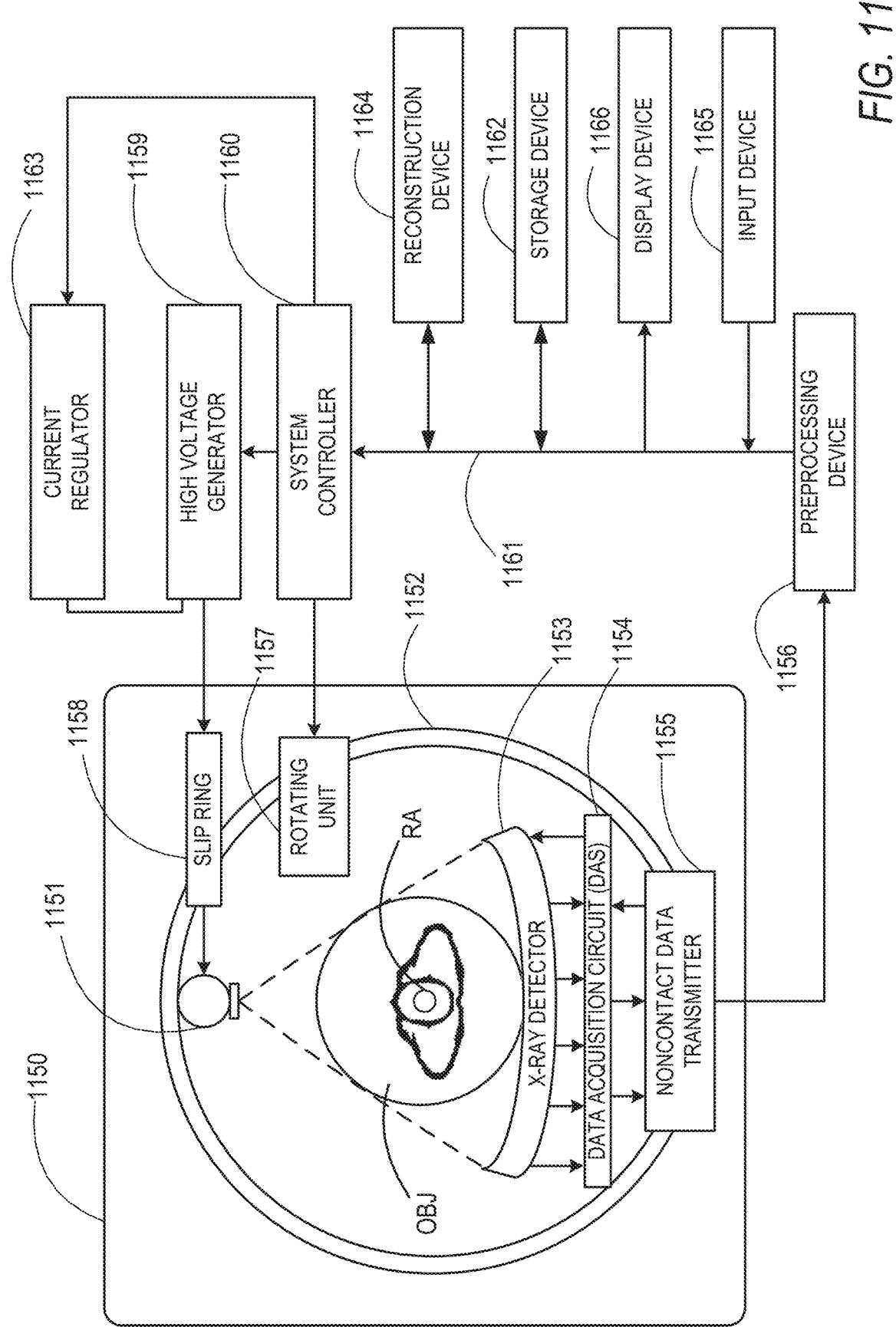
FIG. 11 is a schematic of an implementation of a CT scanner, according to an exemplary embodiment of the present disclosure.

According to an embodiment of the present disclosure, the above-described methods for patient-specific imaging protocols can be implemented as applied to data from a CT apparatus or scanner. FIG. 11 illustrates an implementation of a radiography gantry included in a CT apparatus or scanner. As shown in FIG. 11, a radiography gantry 1150 is illustrated from a side view and further includes an X-ray tube 1151, an annular frame 1152, and a multi-row or two-dimensional-array-type X-ray detector 1153. The X-ray tube 1151 and X-ray detector 1153 are diametrically mounted across an object OBJ on the annular frame 1152, which is rotatably supported around a rotation axis RA. A rotating unit 1157 rotates the annular frame 1152 at a high speed, such as 0.4 sec/rotation, while the object OR is being moved along the axis RA into or out of the illustrated page.

An embodiment of an X-ray CT apparatus according to the present inventions will be described below with reference to the views of the accompanying drawing. Note that X-ray CT apparatuses include various types of apparatuses, e.g., a rotate/rotate-type apparatus in which an X-ray tube and X-ray detector rotate together around an object to be examined, and a stationary/rotate-type apparatus in which many detection elements are arrayed in the form of a ring or plane, and only an X-ray tube rotates around an object to be examined. The present inventions can be applied to either type. In this case, the rotate/rotate-type, which is currently the mainstream, will be exemplified.

The multi-slice X-ray CT apparatus further includes a high voltage generator 1159 that generates a tube voltage applied to the X-ray tube 1151 through a slip ring 1158 so that the X-ray tube 1151 generates X-rays. The X-rays are emitted towards the object OBJ, whose cross-sectional area is represented by a circle. For example, the X-ray tube 1151 having an average X-ray energy during a first scan that is less than an average X-ray energy during a second scan. Thus, two or more scans can be obtained corresponding to different X-ray energies. The X-ray detector 1153 is located at an opposite side from the X-ray tube 1151 across the object OBJ for detecting the emitted X-rays that have transmitted through the object OBJ. The X-ray detector 1153 further includes individual detector elements or units and may be a photon-counting detector. In the fourth-generation geometry system, the X-ray detector 1153 may be one of a plurality of detectors arranged around the object OBJ in a 360° arrangement.

The CT apparatus further includes other devices for processing the detected signals from the X-ray detector 1153. A data acquisition circuit or a Data Acquisition System (DAS) 1154 converts a signal output from the X-ray detector 1153 for each channel into a voltage signal, amplifies the signal, and further converts the signal into a digital signal. The X-ray detector 1153 and the DAS 1154 are configured to handle a predetermined total number of projections per rotation (TPPR).

The above-described data is sent to a preprocessing device 1156, which is housed in a console outside the radiography gantry 1150 through a non-contact data transmitter 1155. The preprocessing device 1156 performs certain corrections, such as sensitivity correction, on the raw data. A memory 1162 stores the resultant data, which is also called projection data at a stage immediately before reconstruction processing. The memory 1162 is connected to a system controller 1160 through a data/control bus 1161, together with a reconstruction device 1164, input device 1165, and display 1166. The system controller 1160 controls a current regulator 1163 that limits the current to a level sufficient for driving the CT system. In an embodiment, the system controller 1160 implements optimized scan acquisition parameters, as described above with reference to FIG. 2A through FIG. 2I.

The detectors are rotated and/or fixed with respect to the patient among various generations of the CT scanner systems. In one implementation, the above-described CT system can be an example of a combined third-generation geometry and fourth-generation geometry system. In the third-generation system, the X-ray tube 1151 and the X-ray detector 1153 are diametrically mounted on the annular frame 1152 and are rotated around the object OBJ as the annular frame 1152 is rotated about the rotation axis RA. In the fourth-generation geometry system, the detectors are fixedly placed around the patient and an X-ray tube rotates around the patient. In an alternative embodiment, the radiography gantry 1150 has multiple detectors arranged on the annular frame 1152, which is supported by a C-arm and a stand.

The memory 1162 can store the measurement value representative of the irradiance of the X-rays at the X-ray detector unit 1153. Further, the memory 1162 can store a dedicated program for executing the CT image reconstruction, material decomposition, and PQR estimation methods including methods described herein.

The reconstruction device 1164 can execute the above-referenced methods, described herein. The reconstruction device 1164 may implement, with reference to FIG. 2A and FIG. 2J, reconstruction according to one or more optimized image reconstruction parameters. Further, reconstruction device 1164 can execute pre-reconstruction processing image processing such as volume rendering processing and image difference processing as needed.

The pre-reconstruction processing of the projection data performed by the preprocessing device 1156 can include correcting for detector calibrations, detector nonlinearities, and polar effects, for example.

Post-reconstruction processing performed by the reconstruction device 1164 can include filtering and smoothing the image, volume rendering processing, and image difference processing, as needed. The image reconstruction process may implement the optimal image reconstruction parameters derived above. The image reconstruction process can be performed using filtered back projection, iterative image reconstruction methods, or stochastic image reconstruction methods. The reconstruction device 1164 can use the memory to store, e.g., projection data, forward projection training data, training images, uncorrected images, calibration data and parameters, and computer programs.

The reconstruction device 1164 can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VDHL, Verilog, or any other hardware description language and the code may be stored in an electronic memory directly within the FPGA or CPLD, or as a separate electronic memory. Further, the memory 1162 can be non-volatile, such as ROM, EPROM, EEPROM or FLASH memory. The memory 1162 can also be volatile, such as static or dynamic RAM, and a processor, such as a microcontroller or microprocessor, can be provided to manage the electronic memory as well as the interaction between the FPGA or CPLD and the memory. In an embodiment, the reconstruction device 1164 can include a CPU and a graphics processing unit (GPU) for processing and generating reconstructed images. The GPU may be a dedicated graphics card or an integrated graphics card sharing resources with the CPU, and may be one of a variety of artificial intelligence-focused types of GPUs, including NVIDIA Tesla and AMD FireStream.

Alternatively, the CPU in the reconstruction device 1164 can execute a computer program including a set of computer-readable instructions that perform the functions described herein, the program being stored in any of the above-described non-transitory electronic memories and/or a hard disc drive, CD, DVD, FLASH drive or any other known storage media. Further, the computer-readable instructions may be provided as a utility application, background daemon, or component of an operating system, or combination thereof, executing in conjunction with a processor, such as a Xeon processor from Intel of America or an Opteron processor from AMD of America and an operating system, such as Microsoft 10, UNIX, Solaris, LINUX, Apple, MAC-OS and other operating systems known to those skilled in the art. Further, CPU can be implemented as multiple processors cooperatively working in parallel to perform the instructions.

In one implementation, the reconstructed images can be displayed on a display 1166. The display 1166 can be an LCD display, CRT display, plasma display, OLED, LED or any other display known in the art.

The memory 1162 can be a hard disk drive, CD-ROM drive, DVD drive, FLASH drive, RAM, ROM or any other electronic storage known in the art.

Obviously, numerous modifications and variations are possible in light of the above teachings. It is therefore to be understood that within the scope of the appended claims, the invention may be practiced otherwise than as specifically described herein.

Embodiments of the present disclosure may also be as set forth in the following parentheticals.

(1) A method for generating a patient-specific imaging protocol using a neural network having been trained to generate at least one probabilistic quality representation corresponding to at least one region of a generated simulated image, comprising receiving, by processing circuitry, scout scan data, the received scout scan data including scout scan information and scout scan parameters, generating, by the processing circuitry, the generated simulated image based on the received scout scan data, scan acquisition parameters, and image reconstruction parameters, deriving, by the processing circuitry, a simulated dose map from the received scout scan data and the scan acquisition parameters, evaluating, by the processing circuitry, a determined image quality of the generated simulated image relative to a predetermined image quality threshold and the derived simulated dose map relative to a predetermined dosage threshold, and generating, by the processing circuitry and based on the evaluating, imaging protocol parameters based on the scan acquisition parameters and the image reconstruction parameters.

(2) The method according to (1), further comprising generating, by the processing circuitry and based on the evaluating, a subsequent generated simulated image based on the received scout scan data, subsequent scan acquisition parameters, and subsequent image reconstruction parameters, deriving, by the processing circuitry, a subsequent simulated dose map from the received scout scan data and the subsequent scan acquisition parameters, evaluating, by the processing circuitry, a determined image quality of the subsequent generated simulated image relative to the predetermined image quality threshold and the subsequent derived simulated dose map relative to the predetermined dosage threshold, and generating, by the processing circuitry and based on the evaluating, subsequent imaging protocol parameters based on the subsequent scan acquisition parameters and the subsequent image reconstruction parameters, the subsequent imaging protocol parameters increasing image quality while reducing radiation exposure.

(3) The method according to either (1) or (2), wherein the determined image quality of the generated simulated image is determined by applying the trained neural network to the generated simulated image, the trained neural network having been trained on scored reference images.

(4) The method according to any one of (1) to (3), wherein the at least one probabilistic quality representation is based on one or more image quality properties including resolution, contrast, artifacts, and noise.

(5) The method according to any one of (1) to (4), wherein the trained neural network is at least one of a disease-specific neural network and a body region-specific neural network.

(6) The method according to any one of (1) to (5), wherein the scan acquisition parameters include x-ray beam energy and tube current.

(7) The method according to any one of (1) to (6), wherein the image reconstruction parameters include reconstruction method and reconstruction kernel.

(8) An apparatus for generating a patient-specific imaging protocol using a neural network having been trained to generate at least one probabilistic quality representation corresponding to at least one region of a generated simulated image, comprising processing circuitry configured to receive scout scan data, the received scout scan data including scout scan information and scout scan parameters, generate the generated simulated image based on the received scout scan data, scan acquisition parameters, and image reconstruction parameters, derive a simulated dose map from the received scout scan data and the scan acquisition parameters, evaluate a determined image quality of the generated simulated image relative to a predetermined image quality threshold and the derived simulated dose map relative to a predetermined dosage threshold, and generate, based on the evaluating, imaging protocol parameters based on the scan acquisition parameters and the image reconstruction parameters.

(9) The apparatus according to (8), wherein the processing circuitry is further configured to generate, based on the evaluating, a subsequent generated simulated image based on the received scout scan data, subsequent scan acquisition parameters, and subsequent image reconstruction parameters, derive a subsequent simulated dose map from the received scout scan data and the subsequent scan acquisition parameters, evaluate a determined image quality of the subsequent generated simulated image relative to the predetermined image quality threshold and the subsequent derived simulated dose map relative to the predetermined dosage threshold, and generate, based on the evaluating, subsequent imaging protocol parameters based on the subsequent scan acquisition parameters and the subsequent image reconstruction parameters, the subsequent imaging protocol parameters increasing image quality while reducing radiation exposure.

(10) The apparatus according to either (8) or (9), wherein the processing circuitry is further configured to apply the trained neural network to the generated simulated image in order to determine the determined image quality of the generated simulated image, the trained neural network having been trained on scored reference images.

(11) The apparatus according to any one of (8) to (10), wherein the processing circuitry is further configured to generate, as the determined image quality of the generated simulated image, at least one image quality metric based on the at least one probabilistic quality representation.

(12) The apparatus according to any one of (8) to (11), wherein the trained neural network is at least one of a disease-specific neural network and a body region-specific neural network.

(13) The apparatus according to any one of (8) to (12), wherein the scan acquisition parameters include x-ray beam energy and tube current.

(14) The apparatus according to any one of (8) to (13), wherein the image reconstruction parameters include reconstruction method and reconstruction kernel.

(15) A non-transitory computer-readable storage medium storing computer-readable instructions that, when executed by a computer, cause the computer to perform a method of generating a patient-specific imaging protocol using a neural network having been trained to generate at least one probabilistic quality representation corresponding to at least one region of a generated simulated image, comprising receiving scout scan data, the received scout scan data including scout scan information and scout scan parameters, generating the generated simulated image based on the received scout scan data, scan acquisition parameters, and image reconstruction parameters, deriving a simulated dose map from the received scout scan data and the scan acquisition parameters, evaluating a determined image quality of the generated simulated image relative to a predetermined image quality threshold and the derived simulated dose map relative to a predetermined dosage threshold, and generating, based on the evaluating, imaging protocol parameters based on the scan acquisition parameters and the image reconstruction parameters.

(16) The non-transitory computer-readable storage medium according to (15), the method further comprising generating, based on the evaluating, a subsequent generated simulated image based on the received scout scan data, subsequent scan acquisition parameters, and subsequent image reconstruction parameters, deriving a subsequent simulated dose map from the received scout scan data and the subsequent scan acquisition parameters, evaluating a determined image quality of the subsequent generated simulated image relative to a predetermined image quality threshold and the subsequent derived simulated dose map relative to a predetermined dosage threshold, and generating, based on the evaluating, subsequent imaging protocol parameters based on the subsequent scan acquisition parameters and the subsequent image reconstruction parameters, the subsequent imaging protocol parameters increasing image quality while reducing radiation exposure.

(17) The non-transitory computer-readable storage medium according to either (15) or (16), wherein the determined image quality of the generated simulated image is determined by applying the trained neural network to the generated simulated image, the trained neural network having been trained on scored reference images.

(18) The non-transitory computer-readable storage medium according to any one of (15) to (17), the method further comprising generating, as the determined image quality, at least one image quality metric based on the at least one probabilistic quality representation.

(19) The non-transitory computer-readable storage medium according to any one of (15) to (18), wherein the neural network is at least one of a disease-specific neural network and a body region-specific neural network.

(20) The non-transitory computer-readable storage medium according to any one of (15) to (19), wherein the scan acquisition parameters include x-ray beam energy and tube current.

(21) A method of training a neural network to generate at least one probabilistic quality representation corresponding to a generated simulated image, comprising receiving, by processing circuitry and from a training database, training data that includes one or more medical images, providing, by the processing circuitry, one of the one or more medical images to an input layer of the neural network, receiving, by the processing circuitry and as an output layer of the neural network, at least one estimated probabilistic quality representation corresponding to the one of the one or more medical images, calculating, by the processing circuitry, a value of a loss function that compares the at least one estimated probabilistic quality representation to an at least one reference probabilistic quality representation associated with the one of the one or more medical images in the training database, and updating, by the processing circuitry, parameters of one or more hidden layers of the neural network based on the calculated value of the loss function.

(22) The method according to (21), wherein the updating includes comparing the calculated value of the loss function to a predetermined threshold value of the loss function, the updating ceasing to update the parameters of the one or more hidden layers of the neural network when the calculated value of the loss function is smaller than the predetermined threshold value of the loss function.

(23) The method according to either (20) or (21), wherein the at least one reference probabilistic quality representation associated with the one of the one or more medical images in the training database is a transformation of at least one scalar score associated with the one of the one or more medical images in the training database.

(24) The method according to any one of (20) to (22), wherein the at least one scalar score associated with the one of the one or more medical images in the training database corresponds to an evaluation, by one or more medical professionals, of the one of the one or more medical images in the training database.

(25) The method according to any one of (20) to (23), wherein the evaluation of the one of the one or more medical images in the training database includes a numerical score of one or more image quality properties of the one of the one or more medical images, the one or more image quality properties including image resolution, image contrast, image artifacts, and image noise.

(26) The method according to any one of (20) to (24), wherein the at least one estimated probabilistic quality representation is an at least one estimated probabilistic quality representation matrix describing a visual map including values of the at least one estimated probabilistic quality representation for at least one region within the one or more medical images.

(27) The method according to any one of (20) to (25), wherein the one or more medical images are at least one of disease-specific and body region-specific.

(28) An apparatus for training a neural network to generate at least one probabilistic quality representation corresponding to a generated simulated image, comprising processing circuitry configured to receive, from a training database, training data that includes one or more medical images, provide one of the one or more medical images to an input layer of the neural network, receive, as an output layer of the neural network, at least one estimated probabilistic quality representation corresponding to the one of the one or more medical images, calculate a value of a loss function that compares the at least one estimated probabilistic quality representation to an at least one reference probabilistic quality representation associated with the one of the one or more medical images in the training database, and update parameters of one or more hidden layers of the neural network based on the calculated value of the loss function.

(29) The apparatus according to (28), wherein the processing circuitry is configured to update the parameters of the one or more hidden layers of the neural network by comparing the calculated value of the loss function to a predetermined threshold value of the loss function and ceasing to update the parameters of the one or more hidden layers of the neural network when the calculated value of the loss function is smaller than the predetermined threshold value of the loss function.

(30) The apparatus according to either (28) or (29), wherein the at least one reference probabilistic quality representation associated with the one of the one or more medical images in the training database is a transformation of at least one scalar score associated with the one of the one or more medical images in the training database.

(31) The apparatus according to any one of (28) to (30), wherein the at least one scalar score associated with the one of the one or more medical images in the training database corresponds to an evaluation, by one or more medical professionals, of the one of the one or more medical images in the training database.

(32) The apparatus according to any one of (28) to (31), wherein the evaluation of the one of the one or more medical images in the training database includes a numerical score of one or more image quality properties of the one of the one or more medical images, the one or more image quality properties including image resolution, image contrast, image artifacts, and image noise.

(33) The apparatus of according to any one of (28) to (32), wherein the at least one estimated probabilistic quality representation is an at least one estimated probabilistic quality representation matrix describing a visual map including values of the at least one estimated probabilistic quality representation for at least one region within the one or more medical images.

(34) The apparatus of according to any one of (28) to (33), wherein the one or more medical images are at least one of disease-specific and body region-specific.

(35) A non-transitory computer-readable storage medium storing computer-readable instructions that, when executed by a computer, cause the computer to perform a training a neural network to generate at least one probabilistic quality representation corresponding to a generated simulated image, comprising receiving, from a training database, training data that includes one or more medical images, providing one of the one or more medical images to an input layer of the neural network, receiving, as an output layer of the neural network, at least one estimated probabilistic quality representation corresponding to the one of the one or more medical images, calculating a value of a loss function that compares the at least one estimated probabilistic quality representation to an at least one reference probabilistic quality representation associated with the one of the one or more medical images in the training database, and updating parameters of one or more hidden layers of the neural network based on the calculated value of the loss function.

(36) The non-transitory computer-readable storage medium according to (35), wherein the updating includes comparing the calculated value of the loss function to a predetermined threshold value of the loss function, the updating ceasing to update the parameters of the one or more hidden layers of the neural network when the calculated value of the loss function is smaller than the predetermined threshold value of the loss function.

(37) The non-transitory computer-readable storage medium according to either (35) or (36), wherein the at least one reference probabilistic quality representation associated with the one of the one or more medical images in the training database is a transformation of at least one scalar score associated with the one of the one or more medical images in the training database.

(38) The non-transitory computer-readable storage medium according to any one of (35) to (37), wherein the at least one scalar score associated with the one of the one or more medical images in the training database corresponds to an evaluation, by one or more medical professionals, of the one of the one or more medical images in the training database.

(39) The non-transitory computer-readable storage medium according to any one of (35) to (38), wherein the evaluation of the one of the one or more medical images in the training database includes a numerical score of one or more image quality properties of the one of the one or more medical images, the one or more image quality properties including image resolution, image contrast, image artifacts, and image noise.

(40) The non-transitory computer-readable storage medium according to any one of (35) to (39), wherein the one or more medical images are at least one of disease-specific and body region-specific.

(41) A method for generating a patient-specific imaging protocol, comprising receiving, by processing circuitry, scout scan data that includes scout scan information and scout scan parameters, generating, by the processing circuitry, a simulated image based on the received scout scan data, scan acquisition parameters, and image reconstruction parameters, applying, by the processing circuitry, a neural network to the generated simulated image to generate at least one probabilistic quality representation, transforming, by the processing circuitry, the generated at least one probabilistic quality representation to, as a determined image quality, a scalar image quality value, deriving, by the processing circuitry, a simulated dose map from the received scout scan data and the scan acquisition parameters, evaluating, by the processing circuitry, the determined image quality of the generated simulated image relative to a predetermined image quality threshold and the derived simulated dose map relative to a predetermined dosage threshold, and generating, by the processing circuitry and when the determined image quality of the generated simulated image satisfies the predetermined image quality threshold and the derived simulated dose map satisfies the predetermined dosage threshold, imaging protocol parameters based on the scan acquisition parameters and the image reconstruction parameters.

(42) The method according to (41), further comprising, when the determined image quality of the generated simulated image does not satisfy the predetermined image quality threshold or the derived simulated dose map does not satisfy the predetermined dosage threshold, generating, by the processing circuitry and based on the evaluating, a subsequent generated simulated image based on the received scout scan data, subsequent scan acquisition parameters, and subsequent image reconstruction parameters, applying, by the processing circuitry, the neural network to the subsequent generated simulated image to generate at least one subsequent probabilistic quality representation, transforming, by the processing circuitry, the generated at least one subsequent probabilistic quality representation to, as a determined image quality of the subsequent generated simulated image, a subsequent scalar image quality value, deriving, by the processing circuitry, a subsequent simulated dose map from the received scout scan data and the subsequent scan acquisition parameters, evaluating, by the processing circuitry, the determined image quality of the subsequent generated simulated image relative to the predetermined image quality threshold and the subsequent derived simulated dose map relative to the predetermined dosage threshold, and generating, by the processing circuitry, based on the evaluating, and when the determined image quality of the subsequent generated simulated image satisfies the predetermined image quality threshold and the subsequent derived simulated dose map satisfies the predetermined dosage threshold, subsequent imaging protocol parameters based on the subsequent scan acquisition parameters and the subsequent image reconstruction parameters, the subsequent imaging protocol parameters increasing image quality while reducing radiation exposure.

(43) The method according to either (41) or (42), wherein the neural network is trained according to at least one reference probabilistic quality representations derived from at least one reference scalar value.

(44) The method according to any one of (41) to (43), wherein the at least one probabilistic quality representation generated by the neural network is based on one or more image quality properties including resolution, contrast, artifacts, and noise.

(45) The method according to any one of (41) to (44), wherein the neural network is at least one of a disease-specific neural network and a body region-specific neural network.

(46) The method according to any one of (41) to (45), wherein the scan acquisition parameters include x-ray beam energy and tube current.

(47) The method according to any one of (41) to (46), wherein the image reconstruction parameters include reconstruction method and reconstruction kernel.

(48) An apparatus for generating a patient-specific imaging protocol, comprising processing circuitry configured to receive scout scan data that includes scout scan information and scout scan parameters, generate a simulated image based on the received scout scan data, scan acquisition parameters, and image reconstruction parameters, apply a neural network to the generated simulated image to generate at least one probabilistic quality representation, transform the generated at least one probabilistic quality representation to, as a determined image quality, a scalar image quality value, derive a simulated dose map from the received scout scan data and the scan acquisition parameters, evaluate the determined image quality of the generated simulated image relative to a predetermined image quality threshold and the derived simulated dose map relative to a predetermined dosage threshold, and generate, when the determined image quality of the generated simulated image satisfies the predetermined image quality threshold and the derived simulated dose map satisfies the predetermined dosage threshold, imaging protocol parameters based on the scan acquisition parameters and the image reconstruction parameters.

(49) The apparatus according to (48), wherein, when the determined image quality of the generated simulated image does not satisfy the predetermined image quality threshold or the derived simulated dose map does not satisfy the predetermined dosage threshold, the processing circuitry is further configured to generate, based on the evaluating, a subsequent generated simulated image based on the received scout scan data, subsequent scan acquisition parameters, and subsequent image reconstruction parameters, apply the neural network to the subsequent generated simulated image to generate at least one subsequent probabilistic quality representation, transform the generated at least one subsequent probabilistic quality representation to, as a determined image quality of the subsequent generated simulated image, a subsequent scalar image quality value, derive a subsequent simulated dose map from the received scout scan data and the subsequent scan acquisition parameters, evaluate the determined image quality of the subsequent generated simulated image relative to the predetermined image quality threshold and the subsequent derived simulated dose map relative to the predetermined dosage threshold, and generate, based on the evaluating and when the determined image quality of the subsequent generated simulated image satisfies the predetermined image quality threshold and the subsequent derived simulated dose map satisfies the predetermined dosage threshold, subsequent imaging protocol parameters based on the subsequent scan acquisition parameters and the subsequent image reconstruction parameters, the subsequent imaging protocol parameters increasing image quality while reducing radiation exposure.

(50) The apparatus according to either (48) or (49), wherein the neural network is trained according to at least one reference probabilistic quality representations derived from at least one reference scalar value.

(51) The apparatus according to any one of (48) to (50), wherein the at least one probabilistic quality representation generated by the neural network is based on one or more image quality properties including resolution, contrast, artifacts, and noise.

(52) The apparatus according to any one of (48) to (51), wherein the neural network is at least one of a disease-specific neural network and a body region-specific neural network.

(53) The apparatus according to any one of (48) to (52), wherein the scan acquisition parameters include x-ray beam energy and tube current.

(54) The apparatus according to any one of (48) to (53), wherein the image reconstruction parameters include reconstruction method and reconstruction kernel.

(55) A non-transitory computer-readable storage medium storing computer-readable instructions that, when executed by a computer, cause the computer to perform a method for generating a patient-specific imaging protocol, comprising receiving scout scan data that includes scout scan information and scout scan parameters, generating a simulated image based on the received scout scan data, scan acquisition parameters, and image reconstruction parameters, applying a neural network to the generated simulated image to generate at least one probabilistic quality representation, transforming the generated at least one probabilistic quality representation to, as a determined image quality, a scalar image quality value, deriving a simulated dose map from the received scout scan data and the scan acquisition parameters, evaluating the determined image quality of the generated simulated image relative to a predetermined image quality threshold and the derived simulated dose map relative to a predetermined dosage threshold, and generating, when the determined image quality of the generated simulated image satisfies the predetermined image quality threshold and the derived simulated dose map satisfies the predetermined dosage threshold, imaging protocol parameters based on the scan acquisition parameters and the image reconstruction parameters.

(56) The non-transitory computer-readable storage medium according to (55), further comprising, when the determined image quality of the generated simulated image does not satisfy the predetermined image quality threshold or the derived simulated dose map does not satisfy the predetermined dosage threshold, generating, based on the evaluating, a subsequent generated simulated image based on the received scout scan data, subsequent scan acquisition parameters, and subsequent image reconstruction parameters, applying the neural network to the subsequent generated simulated image to generate at least one subsequent probabilistic quality representation, transforming the generated at least one subsequent probabilistic quality representation to, as a determined image quality of the subsequent generated simulated image, a subsequent scalar image quality value, deriving a subsequent simulated dose map from the received scout scan data and the subsequent scan acquisition parameters, evaluating the determined image quality of the subsequent generated simulated image relative to the predetermined image quality threshold and the subsequent derived simulated dose map relative to the predetermined dosage threshold, and generating, based on the evaluating and when the determined image quality of the subsequent generated simulated image satisfies the predetermined image quality threshold and the subsequent derived simulated dose map satisfies the predetermined dosage threshold, subsequent imaging protocol parameters based on the subsequent scan acquisition parameters and the subsequent image reconstruction parameters, the subsequent imaging protocol parameters increasing image quality while reducing radiation exposure.

(57) The non-transitory computer-readable storage medium according to either (55) or (56), wherein the neural network is trained according to at least one reference probabilistic quality representations derived from at least one reference scalar value.

(58) The non-transitory computer-readable storage medium according to any one of (55) to (57), wherein the at least one probabilistic quality representation generated by the neural network is based on one or more image quality properties including resolution, contrast, artifacts, and noise.

(59) The non-transitory computer-readable storage medium according to any one of (55) to (58), wherein the neural network is at least one of a disease-specific neural network and a body region-specific neural network.

(60) The non-transitory computer-readable storage medium according to any one of (55) to (59), wherein the scan acquisition parameters include x-ray beam energy and tube current.

(61) The non-transitory computer-readable storage medium according to any one of (55) to (60), wherein the image reconstruction parameters include reconstruction method and reconstruction kernel.

Thus, the foregoing discussion discloses and describes merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variants of the teachings herein, defines, in part, the scope of the foregoing claim terminology such that no inventive subject matter is dedicated to the public.

The invention claimed is:

1. A method for generating a patient-specific imaging protocol using a neural network having been trained to generate at least one probabilistic quality representation corresponding to at least one region of a generated simulated image, comprising:
  receiving, by processing circuitry, scout scan data, the received scout scan data including scout scan information and scout scan parameters;
  generating, by the processing circuitry, the generated simulated image based on the received scout scan data; scan acquisition parameters, and image reconstruction parameters;
  deriving, by the processing circuitry, a simulated dose map from the received scout scan data and the scan acquisition parameters;
  evaluating, by the processing circuitry, a determined image quality of the generated simulated image relative to a predetermined image quality threshold and the derived simulated dose map relative to a predetermined dosage threshold; and generating, by the processing circuitry and based on the evaluating, imaging protocol parameters based on the scan acquisition parameters and the image reconstruction parameters.

2. The method according to claim 1, further comprising
generating; by the processing circuitry and based on the evaluating, a subsequent generated simulated image based on the received scout scan data, subsequent scan acquisition parameters, and subsequent image reconstruction parameters,
deriving, by the processing circuitry, a subsequent simulated dose map from the received scout scan data and the subsequent scan acquisition parameters,
evaluating, by the processing circuitry, a determined image quality of the subsequent generated simulated image relative to the predetermined image quality threshold and the subsequent derived simulated dose map relative to the predetermined dosage threshold, and
generating, by the processing circuitry and based on the evaluating, subsequent imaging protocol parameters based on the subsequent scan acquisition parameters and the subsequent image reconstruction parameters, the subsequent imaging protocol parameters increasing image quality while reducing radiation exposure.

3. The method according to claim 1, wherein the determined image quality of the generated simulated image is determined by applying the trained neural network to the generated simulated image, the trained neural network having been trained on scored reference images.

4. The method according to claim 1, wherein the at least one probabilistic quality representation is based on one or more image quality properties including resolution, contrast, artifacts, and noise.

5. The method according to claim 1, wherein the trained neural network is at least one of a disease-specific neural network and a body region-specific neural network.

6. The method according to claim 1, wherein the scan acquisition parameters include x-ray beam energy and tube current.

7. The method according to claim 1, wherein the image reconstruction parameters include reconstruction method and reconstruction kernel.

8. An apparatus for generating a patient-specific imaging protocol using a neural network having been trained to generate at least one probabilistic quality representation corresponding to at least one region of a generated simulated image, comprising:
processing circuitry configured to
receive scout scan data, the received scout scan data including scout scan information and scout scan parameters,
generate the generated simulated image based on the received scout scan data, scan acquisition parameters, and image reconstruction parameters,
derive a simulated dose map from the received scout scan data and the scan acquisition parameters,
evaluate a determined image quality of the generated simulated image relative to a predetermined image quality threshold and the derived simulated dose map relative to a predetermined dosage threshold, and
generate, based on the evaluating, imaging protocol parameters based on the scan acquisition parameters and the image reconstruction parameters.

9. The apparatus according to claim 8, wherein the processing circuitry is further configured to
generate, based on the evaluating, a subsequent generated simulated image based on the received scout scan data, subsequent scan acquisition parameters, and subsequent image reconstruction parameters,
derive a subsequent simulated dose map from the received scout scan data and the subsequent scan acquisition parameters,
evaluate a determined image quality of the subsequent generated simulated image relative to the predetermined image quality threshold and the subsequent derived simulated dose map relative to the predetermined dosage threshold, and
generate, based on the evaluating, subsequent imaging protocol parameters based on the subsequent scan acquisition parameters and the subsequent image reconstruction parameters, the subsequent imaging protocol parameters increasing image quality while reducing radiation exposure.

10. The apparatus according to claim 8, wherein the processing circuitry is further configured to
apply the trained neural network to the generated simulated image in order to determine the determined image quality of the generated simulated image, the trained neural network having been trained on scored reference images.

11. The apparatus according to claim 8, wherein the processing circuitry is further configured to
generate, as the determined image quality of the generated simulated image, at least one image quality metric based on the at least one probabilistic quality representation.

12. The apparatus according to claim 8, wherein the trained neural network is at least one of a disease-specific neural network and a body region-specific neural network.

13. The apparatus according to claim 8, wherein the scan acquisition parameters include x-ray beam energy and tube current.

14. The apparatus according to claim 8, wherein the image reconstruction parameters include reconstruction method and reconstruction kernel.

15. A non-transitory computer-readable storage medium storing computer-readable instructions that, when executed by a computer, cause the computer to perform a method of generating a patient-specific imaging protocol using a neural network having been trained to generate at least one probabilistic quality representation corresponding to at least one region of a generated simulated image, comprising:
receiving scout scan data, the received scout scan data including scout scan information and scout scan parameters;
generating the generated simulated image based on the received scout scan data, scan acquisition parameters; and image reconstruction parameters;
deriving a simulated dose map from the received scout scan data and the scan acquisition parameters;
evaluating a determined image quality of the generated simulated image relative to a predetermined image quality threshold and the derived simulated dose map relative to a predetermined dosage threshold; and
generating, based on the evaluating, imaging protocol parameters based on the scan acquisition parameters and the image reconstruction parameters.

16. The non-transitory computer-readable storage medium according to claim 15, the method further comprising
   generating, based on the evaluating, a subsequent generated simulated image based on the received scout scan data, subsequent scan acquisition parameters, and subsequent image reconstruction parameters,
   deriving a subsequent simulated dose map from the received scout scan data and the subsequent scan acquisition parameters,
   evaluating a determined image quality of the subsequent generated simulated image relative to a predetermined image quality threshold and the subsequent derived simulated dose map relative to a predetermined dosage threshold, and
   generating, based on the evaluating, subsequent imaging protocol parameters based on the subsequent scan acquisition parameters and the subsequent image reconstruction parameters, the subsequent imaging protocol parameters increasing image quality while reducing radiation exposure.

17. The non-transitory computer-readable storage medium according to claim 15, wherein the determined image quality of the generated simulated image is determined by
   applying the trained neural network to the generated simulated image, the trained neural network having been trained on scored reference images.

18. The non-transitory computer-readable storage medium according to claim 15, the method further comprising
   generating, as the determined image quality, at least one image quality metric based on the at least one probabilistic quality representation.

19. The non-transitory computer-readable storage medium according to claim 15, wherein the neural network is at least one of a disease-specific neural network and a body region-specific neural network.

20. The non-transitory computer-readable storage medium according to claim 15, wherein the scan acquisition parameters include x-ray beam energy and tube current.

* * * * *